US005885967A

United States Patent [19]
Schacht et al.

[11] Patent Number: 5,885,967
[45] Date of Patent: Mar. 23, 1999

[54] ANTITHROMBOTIC AGENTS

[75] Inventors: Aaron L. Schacht; Gerald F. Smith; Michael R. Wiley, all of Indianapolis, Ind.

[73] Assignee: Eli Lilly and Company, Indianapolis, Ind.

[21] Appl. No.: 206,351

[22] Filed: Mar. 4, 1994

[51] Int. Cl.⁶ .................... C07K 5/00; H61K 38/00; H61K 31/40; C07D 211/60

[52] U.S. Cl. .................... 514/19; 514/213; 514/313; 514/314; 514/318; 514/323; 514/326; 514/329; 514/330; 514/331; 514/412; 514/414; 514/415; 514/419; 514/423; 530/332; 540/593; 540/594; 546/164; 546/171; 546/174; 546/175; 546/225; 546/226; 546/245; 548/452; 548/467; 548/469; 548/483; 548/484; 548/486; 548/492; 548/535

[58] Field of Search .................... 546/225, 220, 546/164, 171, 174, 175, 295; 548/492, 452, 467, 469, 483, 484, 481; 540/593, 594; 514/213, 313, 314, 318, 323, 326, 329, 330, 331, 412, 414, 415, 419, 423, 19; 530/332

[56] References Cited

U.S. PATENT DOCUMENTS

| | | |
|---|---|---|
| 4,316,889 | 2/1982 | Bajusz et al. . |
| 4,346,078 | 8/1982 | Bajusz et al. . |
| 4,399,065 | 8/1983 | Bajusz et al. . |
| 4,478,745 | 10/1984 | Bajusz et al. . |
| 4,703,036 | 10/1987 | Bajusz et al. . |
| 5,053,392 | 10/1991 | Klein et al. . |
| 5,153,176 | 10/1992 | Abe et al. ............. 514/18 |
| 5,202,416 | 4/1993 | Steuber et al. . |
| 5,204,323 | 4/1993 | Findlay et al. . |
| 5,250,660 | 10/1993 | Shuman et al. . |
| 5,252,566 | 10/1993 | Shuman ............. 514/210 |
| 5,380,713 | 1/1995 | Balasubramanian et al. ............. 514/18 |
| 5,416,093 | 5/1995 | Shuman ............. 514/307 |
| 5,430,023 | 7/1995 | Gesellchen et al. ............. 514/18 |
| 5,436,229 | 7/1995 | Ruterbories et al. ............. 514/18 |
| 5,439,888 | 8/1995 | Shuman et al. ............. 514/18 |
| 5,484,772 | 1/1996 | Sall et al. ............. 514/18 |
| 5,488,037 | 1/1996 | Sall et al. ............. 514/19 |

FOREIGN PATENT DOCUMENTS

| | | | |
|---|---|---|---|
| A-16380/95 | 4/1995 | Australia ............. C07K 5/065 |
| A-21801/95 | 6/1995 | Australia ............. C07K 5/065 |
| 0 503 203 | 9/1962 | European Pat. Off. . |
| 0 293881 | 12/1988 | European Pat. Off. . |
| 0 369 391 | 5/1990 | European Pat. Off. . |
| 0 397 427 | 11/1990 | European Pat. Off. . |
| 0 399 688 | 11/1990 | European Pat. Off. . |
| 0 410 411 | 1/1991 | European Pat. Off. . |
| 0 479 489 | 4/1992 | European Pat. Off. . |
| 0 526 877 | 8/1992 | European Pat. Off. . |
| 504 064 | 9/1992 | European Pat. Off. ............. C07K 5/06 |
| 0 529 568 | 3/1993 | European Pat. Off. . |
| 0 530 167 | 3/1993 | European Pat. Off. . |
| 0 542 525 | 5/1993 | European Pat. Off. . |
| 0 601 459 | 6/1994 | European Pat. Off. . |
| 648 780 | 8/1994 | European Pat. Off. ............. C07K 5/06 |
| WO93/08211 | 4/1993 | WIPO . |
| WO 93/11152 | 6/1993 | WIPO . |
| WO 93/15756 | 8/1993 | WIPO . |
| WO 94/29335 | 12/1994 | WIPO ............. C07K 5/06 |
| WO 94/29336 | 12/1994 | WIPO ............. C07K 5/06 |
| WO 95/09634 | 4/1995 | WIPO ............. C07F 5/02 |
| WO 95/09858 | 4/1995 | WIPO ............. C07F 5/02 |
| WO 95/09859 | 4/1995 | WIPO ............. C07F 5/02 |

OTHER PUBLICATIONS

Bajusz, S., et al., *J. Med. Chem.*, 1990, 33, 1729–1735.
Fareed, J., et al., *Annals N.Y. Academy of Sciences* 1981, 765–784.
Shuman, et al., Proceedings of the Twelfth American Peptide Symposium, Jun. 16–21, 1991.
Wilson, et al., American Heart Association, Nov. 11–14, 1991, Anaheim Convention Center, Anaheim, CA.
Bajusz, et al., *Int. J. Peptide Res.*, 12, 1978, 217–221.
Gesellchen, et al., Tenth American Peptide Symposium, May 23–28, 1987, St. Louis, MO.
K.D. Kurz, T. Smith, R.A. Moore, and B.W. Main. Comparison of Thrombin Inhibitors in Rat Models of Thrombosis and Thrombolysis. FASEB Journal, vol. 5 (No.4), 1991.
Tomori, et al., *Chromatographia* vol. 19, 437–442 (1984).
Dayhoff, *Atlas of Protein Sequence and Structure 5*, pp. 85–89 (1972).
Shuman, et al., *J. Med. Chem.*, 36(3), 314–319 (1993).
Jackson, et al., *J. Cardiovasc. Pharmacol.*, 21(4), 587–594 (1993).
Cheng, et al., *Tetrahedron Lett.* 32 (49), 7333–7336 (1991).
Bagdy, et al., *Thrombosis and Haemostasis*, 68(2), 125–129 (1992).
*Thrombosis and Haemostasis*, 65, 1289, No. 2150–2151 and 2152 (1991).
Bagdy, et al., *Thrombosis and Haemostasis*, 67(3), 325–330 (1992).
Bagdy, et al., *Thrombosis and Haemostasis*, 67(3), 357–365 (1992).
Balasubramanian, et al., *J. Med. Chem.*, 36, 300–303 (1993).
Kurz et al., Antithrombotic Efficacy in the Rat After Intravenous and Oral Administration of a Direct Inhibitor of Thrombin FASEB, Mar. 28–Apr. 1, 1993.
Iwanowicz, et al., *Bioorg. Med. Chem. Lett.*, 2(12), 1607–1612 (1992).
Barabas, et al., *Blood Coagul. Fibrin.*, 4, 243–248(1993).

(List continued on next page.)

*Primary Examiner*—C. Warren Ivy
*Assistant Examiner*—Raymond Covington
*Attorney, Agent, or Firm*—Thomas E. Jackson; Robert A. Conrad; David E. Boone

[57] ABSTRACT

This invention relates to peptide derivatives, pharmaceutical formulations containing those compound and methods of their use as thrombin inhibitors.

9 Claims, No Drawings

OTHER PUBLICATIONS

Jackson, et al., Conjunctive Therapy with the Thrombin Inhibitor, LY 294468, and Aspirin Produced Enhanced Antireocclusive Activity When Used in a Canine Model of Streptokinase–Induced Coronary Thrombolysis, *The Pharmacologist*, 35(3), 207 (1993).

Pozsgay, et al., Study of the Specificity of Thrombin with Tripeptidyl–p–nitroanilide Substrates, *Eur. J. Biochem.*, 115, 491–495 (1981).

Grzon, et al., Synthesis and Some Pharmacological Properties of Oxytocin and Vasopressin Analogues with Sarcosine or N–Methyl–L–alanine in Position 7, *J. Med. Chem.*, 26, 555–559 (1983).

Bataille, et al., The L–Proline Residue as a 'Break–point' in the Co–ordination of Metal–Peptide Systems, *J. Chem. Soc., Chem. Commun.*, 231–232 (1984).

Claeson, et al., Proceedings of the Twelfth American Peptide symposium, Jun. 16–21, 1991, Cambridge, MA, pp. 822–823 and 824–825.

Smith, G. F., Shuman, R. T. Gesellchen, P.D., Craft, T.J., Gifford, P., Kurz, K.D., Jackson, C.V., Sandusky, G.E., and P.D. Williams, A New Family of Thrombin Inhibitors with Improved Specificity and Therapeutic Index. (Submitted to the American Heart Association, Oct., 1991, Circulation Oct., 1991, vol. 84, II–579, 1991).

Jackson, V., Wilson, H., Frank, J., Crowe, V., Craft, T., and G. Smith. The Thrombin Inhibitor, Methyl–D–Phe–Pro–Arginal—An Effective Adjunct to Coronary Artery Thrombolysis in the Anesthetized Dog. FASEB J. 5(4)A521 (1991).

Crowe, V., Frank, J., Wilson, H., Coffman, B., Smith, G., and V. Jackson. Anticoagulant and Antithrombotic Efficacy of the Novel Thrombin Inhibitor Methyl–D–Phg–Pro–Arginal in a Canine Model of Coronary Thrombosis. FASEB J. 5(4)A521 (1991).

Wilson, H., Frank J., Crowe, V., Coffman, B., Smith, G., Shuman, R., and V. Jackson. Anticoagulant and Antithrombotic Efficacy of the Novel Thrombin Inhibitor, Methyl–D–Phg–Pro–Arginal, in a Canine Model of Coronary Thrombosis (Arteriosclerosis and Thrombosis, 11(5), Oct., 1991).

Jackson, V., Wilson, H., Frank, J., Crowe, V., Coffman, B., Shuman, R., and G. Smith. The Novel Thrombin Inhibitor Methyl–D–Phg–Pro–Arginal: An Effective Conjunctive Agent to Coronary Artery Thrombolysis in the Anesthetized Dog. (Arteriosclerosis and Thrombosis, 11(5), Oct., 1991).

Shuman, R.T., Rothenberger, R.B., Campbell, C.S., Smith, G.F., Jackson, C.V., Kurz, K.D., and P.D. Gesellchen. Prevention of Reocclusion by a Thrombin Inhibitor. (American Peptide Symposium, Jun., 1991, pp. 799–800).

Shuman, R.T., Rothenberger, R.B., Campbell, C.S., Smith, G.F., Jackson, C.V., Kurz, K.D., and P.D. Gesellchen. A Series of Highly Active Serine Proteinase Inhibitors. (American Peptide Symposium, Jun. 1991, pp. 801–802).

Jackson, C.V., Frank, J.D., Crowe, V.G., Craft, T.J., and G.F. Smith. Assessment of the Anticoagulant and Antithrombotic Efficacy of the Thrombin Inhibitor, Boc–Phe–Pro–Arginal, in a Canine Model of Coronary Thrombosis. *Arteriosclerosis*, 10 922A (1990).

Jackson, C.V., Frank, J.D., Crowe, V.G., Craft, T.J., and G.F. Smith. The Thrombin Inhibitor, Boc–D–Phe–Pro–Arginal. An Effective Adjunct to Coronary Artery Thrombolysis in the Anesthetized Dog. *Arteriosclerosis*, 10 923a (1990).

Shackelford, K.A., Tanzer, R.L., Shuman, R., Gesellchen, P.D., Grindey, G.B., Sundboom, J.L., Smith, G.F., and R.L. Merriman. Inhibition of Spontaneous Metastasis by Boc–D–Phe–Pro–Arginal. American Association for Cancer Research, San Francisco, 1989. *Proc. Am. Assn. Cancer Res.*, 30 86, 1989.

Neubauer, B.L., Clemens, J.A., Gesellchen, P.D., Hirsch, K.S., Hoover, D.M., Merriman, R.L., and G.F. Smith. Endocrine Characterization and Sensitivity of the PAIII Prostatic Adenocarcinoma in Male Lobund–Wistar (LW) Rats to Anti–Fibrin Agents. American Association for Cancer Research. New Orleans, May 1988, *Proc. Am. Assn. Cancer Res.*, 29 240 (1988).

Neubauer, B.L., Best, K.L., Gesellchen, P.D., Goode, R.L., Merriman, R.L., Tanzer, L.R., Shaar, C.J., Shuman, R., Sundboom, Pro–Arginal on the Metastasis of the PAIII Prostatic Adenocarcinoma in Male Lobund Wistar (LW) Rats. American Urological Association. Boston, May 1988, *J. Urol.*, 139 175A (1988).

Gesellchen, P.D., Smith, G.F., et al., Anticoagulant, Antithrombotic, and Antimetastatic Effects of a Serine Proteinase Inhibitor. 10th American Peptide Symposium, Washington University, St. Louis, MO (1987).

Smith, G.F., Sundboom, J.L., Best, K., Gesellchen, P.D., Merriman, R.L., Shuman, R., and Neubauer, B.L. Heparin, Boc–D–Phe–Pro–Arginal, and Warfarin (Fibrin Antagonists) Inhibit Metastasis in an In Vivo Model. American Chemical Society National Meeting. Abstract Biol 70 Biochemistry (1987).

Stueber, et al., Proc. of the 13th American Peptide Symposium, Jun. 20–25, 1993.

Stürzebecher, et al., XIVth Congress of the International Society on Thrombosis and Hemostasis, Jul. 4–9, 1993.

Simoons et al., *Circulation*, 90, I–231, Abstr. 1241 (1994).

Iwanowicz et al., *J. Med. Chem.*, 1994, 37, 2122–2124.

ANTITHROMBOTIC AGENTS

BACKGROUND OF THE INVENTION

This invention relates to thrombin inhibitors which are useful anticoagulants in mammals. In particular it relates to peptide derivatives having high antithrombotic activity, anticoagulant activity, and oral bioavailability.

The process of blood coagulation, thrombosis, is triggered by a complex proteolytic cascade leading to the formation of thrombin. Thrombin proteolytically removes activation peptides from the Aα-chains and Bβ-chains of fibrinogen, which is soluble in blood plasma, initiating insoluble fibrin formation.

Anticoagulation is currently achieved by the administration of heparins and coumarins.

Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because surface-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the post-translational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest in small synthetic peptides that are recognized by proteolytic enzymes in a manner similar to that of natural substrates has grown. Tripeptide aldehydes such as D-Phe-Pro-Arg-H, Boc-D-Phe-Pro-Arg-H, and D-MePhe-Pro-Arg-H, Bajusz et al., *J. Med. Chem.*, 33, 1729–1735 (1990) demonstrate potent direct inhibition of thrombin. Many investigators have synthesized analogs in an effort to develop pharmaceutical agents, for example Shuman et al., *J. Med. Chem.*, 36, 314–319 (1993).

Although the heparins and coumarins are effective anticoagulants, and no drug has yet emerged from the known tripeptide aldehydes, and despite the continuing promise for this class of compounds, there exists a need for anticoagulants that act selectively on thrombin, and independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that may have high bioavailability following oral administration.

Accordingly, it is a primary object of the present invention to provide novel peptide derivatives that are potent thrombin inhibitors useful as anticoagulants.

Other objects features and advantages will be apparent to those skilled in the art from the following description and claims.

SUMMARY OF THE INVENTION

The present invention provides thrombin inhibiting compounds having the Formula

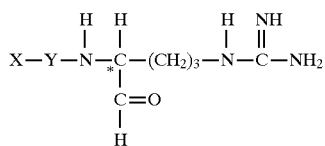

wherein

X is prolinyl, homoprolinyl,

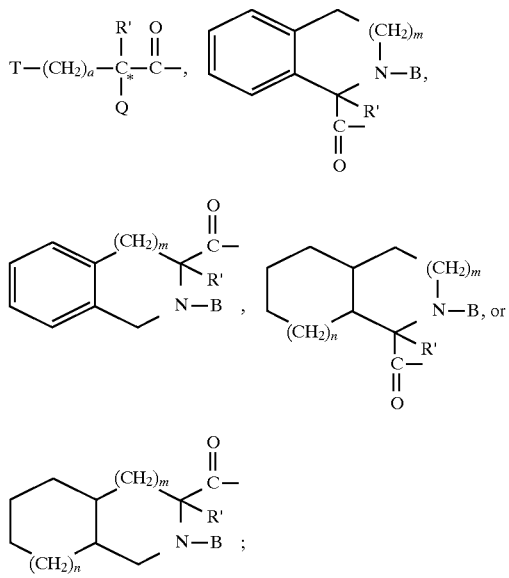

T is $C_3$–$C_8$ cycloalkyl, $C_1$–$C_8$ alkyl,

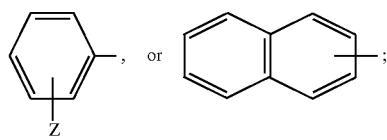

a is 0 or 1;

Q is —OH, $C_1$–$C_4$ alkoxy, or —NH—A;

A is $C_1$–$C_4$ alkyl, R"$SO_2$—, R"OC(O)—, R"C(O)—, HOOCSO$_2$—, HOOCC(O)—, or —(CH$_2$)$_g$—COOH;

g is 1, 2, or 3;

B is hydrogen or $C_1$–$C_4$ alkyl;

R'is hydrogen or $C_1$–$C_4$ alkyl;

R"is $C_1$–$C_4$ alkyl, $C_1$–$C_4$ perfluoroalkyl, —(CH$_2$)$_d$—COOH, or unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

d is 1, 2, or 3;
m is 0, 1, or 2;
n is 0, 1, or 2;

R is $C_1$-$C_6$ alkyl, $C_3$-$C_8$ cycloalkyl, or —$(CH_2)_p$—L—$(CH_2)_q$—T'; where p is 0, 1, 2, 3, or 4, L is a bond, —O—, —S—, or —NH—, q is 0, 1, 2 or 3, and T' is hydrogen, $C_1$-$C_4$ alkyl, $C_3$-$C_8$ cycloalkyl, —COOH, —$CONH_2$, or Ar, where Ar is unsubstituted or substituted aryl as defined above for R''; and Z is hydrogen, $C_1$-$C_4$ alkyl, $C_1$-$C_4$ alkoxy, hydroxy, halo, or $R_aSO_2NH$—, where $R_a$ is $C_1$-$C_4$ alkyl;

and pharmaceutically acceptable salts and solvates thereof.

In addition to the compounds of Formula I, the present invention provides pharmaceutical formulations comprising a compound of Formula I in association with a pharmaceutically acceptable carrier, diluent or excipient.

The present invention also provides a method of inhibiting thrombosis in mammals comprising administering to a mammal in need of treatment, an antithrombotic dose of a compound of Formula I.

The present invention further provides a method of inhibiting thrombin comprising administering to a mammal in need of treatment, a thrombin inhibiting dose of a compound of Formula I.

DETAILED DESCRIPTION OF THE INVENTION

This invention relates to new inhibitors of thrombin, pharmaceutical compositions containing the compounds as active ingredients, and the use of the compounds as anticoagulants for prophylaxis and treatment of thromboembolic diseases such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process.

The term "alkyl" by itself or as part of another substituent means a straight or branched chain alkyl radical having the stated number of carbon atoms such as methyl, ethyl, n-propyl, isopropyl, n-butyl, t-butyl, isobutyl and sec-butyl. The term "perfluoroalkyl" by itself or as part of another substituent means a straight or branched chain alkyl radical having the stated number of carbon atoms in which each hydrogen atom is replaced with a fluorine atom such as trifluoromethyl, perfluoroethyl, perfluoro-n-propyl, perfluoroisopropyl, perfluoro-n-butyl, perfluoro-t-butyl, perfluoroisobutyl and perfluoro-sec-butyl.

The term "$C_3$-$C_8$ cycloalkyl" refers to the saturated alicyclic rings of three to eight carbon atoms such as cyclopropyl, methylcyclopropyl, cyclobutyl, cyclopentyl, cyclohexyl, 4-methylcyclohexyl, cyclooctyl, and the like.

The term "alkoxy" means a straight or branched chain alkyl radical having the stated number of carbon atoms bonded to the parent moiety by an oxygen atom. The term "halo" means chloro, fluoro, bromo or iodo. The term "acetyl" means $CH_3$—C(O)—. The term "t-butyloxycarbonyl" means $(CH_3)_3$C—O—C(O)— and is abbreviated "Boc". The term "benzyloxycarbonyl" means $C_6H_5CH_2$—O—C(O)— and is abbreviated "Cbz".

The term "5- or 6-membered heterocyclic ring" means any 5- or 6-membered ring that will afford a stable structure containing one or two nitrogen atoms; one sulfur atom; one oxygen atom; one nitrogen and one sulfur atom; or one nitrogen and one oxygen atom. The 5-membered ring has one or two double bonds and the 6-membered ring has two or three double bonds. Such heterocyclic systems include furyl, thienyl, pyrrolyl, pyrazolyl, oxazolyl, isoxazolyl, thiazolyl, isothiazolyl, pyranyl, pyridinyl, pyrimidinyl, pyrazinyl, oxazinyl and thiazinyl.

The term "9- or 10-membered heterocyclic ring" means any bicyclic group in which any of the above 5- or 6-membered rings is fused to a benzene ring or another 6-membered heterocyclic ring as defined above that will afford a stable structure. These heterocyclic systems include indolyl, benzothienyl, benzofuryl, benzoxazolyl, benzoisoxazolyl, benzopyrazolyl, quinolinyl, isoquinolinyl, benzimidazolyl and benzothiazolyl.

It will be appreciated that many of the above heterocycles may exist in tautomeric forms. All such forms are included within the scope of this invention.

All of the aryl groups listed for the definition of Ar are unsubstituted or substituted with one or two substituents that will afford a stable structure independently selected from halo, hydroxyl, $C_1$-$C_4$ alkyl, $C_1$-$C_4$ alkoxy, amino (—$NH_2$), mono($C_1$-$C_4$ alkyl)amino, —$(CH_2)_k$COOH, mercapto, —$S(O)_h$($C_1$-$C_4$ alkyl), —$NHS(O)_h$($C_1$-$C_4$ alkyl), —NHC(O)($C_1$-$C_4$ alkyl), —$S(O)_hNH_2$, —$S(O)_hNH(C_1$-$C_4$ alkyl), or —$S(O)_hN(C_{1-C4}$ alkyl)$_2$, h is 0, 1 or 2, and k is 0, 1, 2, 3, or 4. One particularly preferred such substituent is 1-methylindol-2-oyl.

In the representation of Formula I, the carbonyl functionality of group X is attached to the amine functionality of the Y group. The carbonyl functionality of Y is then attached to the amino group drawn in Formula I.

The group,

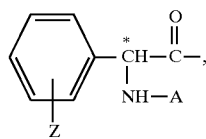

wherein Z and A are both hydrogen, is referred to at times herein as phenylglycyl and abbreviated Phg. Compounds wherein A is, e.g., methyl, are referred to as the $N^\alpha$methyl-phenylglycyl group and abbreviated MePhg. Substituted compounds wherein z is other than hydrogen are referred to by the type and position of the substituent group, e.g., 3'-chlorophenylglycyl or Phg(3-Cl).

The group,

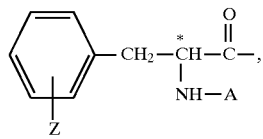

The group Z, where Z and A are both hydrogen, is referred to at times herein as phenylalanyl and abbreviated Phe. Compounds wherein A is, e.g., methyl, are referred to as the $N^\alpha$methyl-phenylalanyl group and abbreviated MePhe. Substituted compounds wherein Z is other than hydrogen are referred to by the type and position of the substituent group, e.g., 3'-chlorophenylalanyl or Phe(3-Cl).

The groups

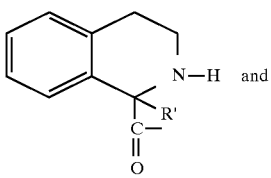 and

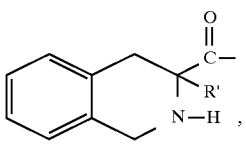

when R' is hydrogen, are referred to at times herein as 1- and 3-tetrahydro-isoquinolinecarboxylate, respectively, and are respectively abbreviated 1-Tiq and 3-Tiq.

The groups

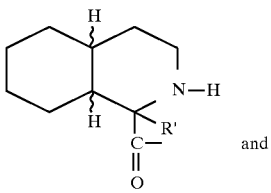 and

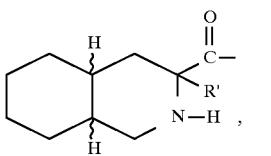

when R' is hydrogen, are referred to at times herein as 1- and 3-perhydro-isoquinolinecarboxylate, respectively, and are respectively abbreviated 1-Piq and 3-Piq. As indicated by the crooked lines, various ring fusion isomers of these substituents exist—this invention contemplates any individual isomer and combinations thereof.

The asterisks in Formula I and substituent Y denote a chiral center that is (L). The asterisk in substituent X denotes a chiral center that is (D) or (DL).

In addition, diastereomers may exist depending upon branching of alkyl substituents. The compounds of the present invention include mixtures of two or more diastereomers as well as each individual isomer.

Preferred compounds of the present invention are those compounds of Formula I where X is

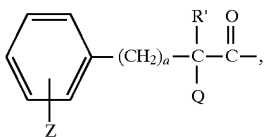

homoprolinyl, 1- or 3-Tiq, or 1- or 3-Piq, and R is $C_1$–$C_6$ alkyl or —$(CH_2)_p$—L—$(CH_2)_q$—Ar, and pharmaceutically acceptable salts and solvates thereof. In particular, compounds wherein Q is NHA and A is a sulfonamide (e.g., A=R"$SO_2$—), R' is hydrogen, and B is hydrogen are all preferred. Also, those compounds wherein R is lower alkyl (e.g., methyl, ethyl, or n-propyl) are preferred. Also preferred are those compounds wherein R is phenylalkyl, e.g., phenylethyl.

As mentioned above, the invention includes pharmaceutically acceptable salts of the compounds defined by the above Formula I. A particular compound of this invention can possess one or more sufficiently basic functional groups, and accordingly react with any of a number of inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid, hydrobromic acid and sulfuric acid.

The compounds of the present invention are known to form hydrates and solvates with appropriate solvents. Preferred solvents for the preparation of solvate forms include water, alcohols, tetrahydrofuran, DMF, and DMSO. Preferred alcohols are methanol and ethanol. Other appropriate solvents may be selected based on the size of the solvent molecule. Small solvent molecules are preferred to facilitate the corresponding solvate formation. The solvate or hydrate is typically formed in the course of recrystallization or in the course of salt formation. One useful reference concerning solvates is Sykes, Peter, A Guidebook to Mechanism in Organic Chemistry, 6th Ed (1986, John Wiley & Sons, New York). As used herein, the term "solvate" includes hydrate forms, such as monohydrates and dihydrates.

The compounds of Formula I are prepared by known methods of peptide coupling. According to one such method the acid P—X'—COOH, where —X'—C(O)— has the same meaning as —X— as defined in Formula I, and P is an amino protecting group, if necessary, is coupled with a carboxy protected substituted glycine to form the dipeptide (a). The carboxy protecting ester group of the glycine moiety is then removed (deblocked or de-esterified) and the free acid form of the dipeptide (b) is coupled with the lactam form of arginine (d). The above reaction sequence is illustrated by the following Scheme 1:

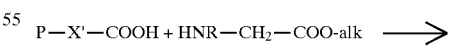

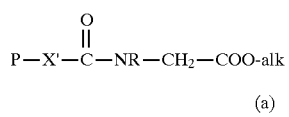

(a)

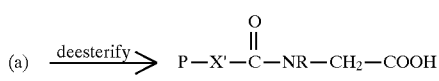

(b)

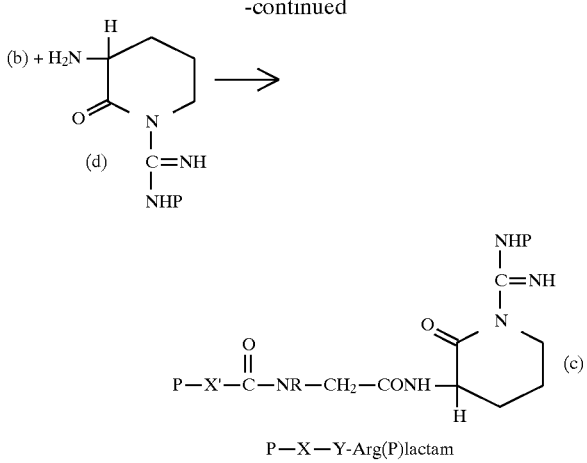

wherein P represents an amino protecting group and alk is lower alkyl or some similar carboxylic acid protecting group.

The coupled Arg (P) lactam product (c) is reacted with a hydride reducing agent, preferably lithium aluminum hydride or lithium tri-tert-butoxyaluminohydride, in an inert solvent or mixture of solvents to reduce the lactam ring and provide the tripeptide in the arginine aldehyde form represented by the formula

wherein (P) represents amino protecting groups.

The protecting groups are removed by procedures known to those skilled in the art such as hydrogenation over a metal catalyst.

The lactam form of arginine is obtained by intramolecular coupling of amino protected arginine [Arg-OH]. For example, Boc-Arg(Cbz)OH represented by the formula

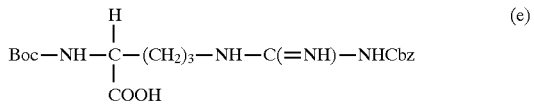

where Boc is t-butyloxycarbonyl and Cbz is benzyloxycarbonyl, is first converted to an active ester form, such as an active mixed anhydride, with a chloroformate ester, e.g. ethyl chloroformate to isobutyl chloroformate. The ester formation is carried out in the presence of a tertiary amine such as N-methylmorpholine. Addition of further or another tertiary amine base, such as triethylamine or diisopropylethylamine, effects the internal acylation to provide the lactam form of the di-amino protected arginine as shown below

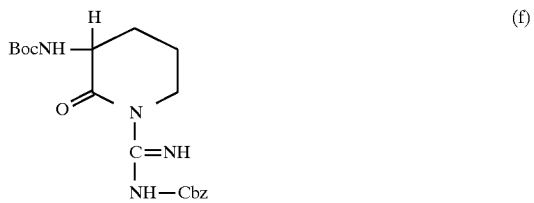

Prior to use in the coupling with the P—X' (C=O)—NR—CH$_2$—COOH as shown in the above scheme, the Boc or other amine protecting group is selectively removed with trifluoroacetic acid or anhydrous HCl to provide the requisite free amino group.

The coupling of an P—X'—COOH compound with a glycine carboxylic ester, is carried out by first protecting the amino group of the amino acid, if any. Conventional amino protecting groups commonly used for temporary protection or blocking of the amino group are employed.

The amino-protecting group refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, t-butoxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl) isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)ethoxycarbonyl, 9-fluoroenylmethoxycarbonyl ("FMOC"), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy) benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group, and the like amino-protecting groups. The species of amino-protecting group employed is not critical so long as the derivatized amino group is stable to the condition of subsequent reaction(s) on other positions of the molecule and can be removed at the appropriate point without disrupting the remainder of the molecule. Preferred amino-protecting groups are the benzyloxycarbonyl, allyloxycarbonyl, t-butoxycarbonyl, and trityl groups. Similar amino-protecting groups used in the cephalosporin, penicillin and peptide art are also embraced by the above terms. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

In carrying out the coupling reaction an ester protecting group for glycine is employed which is removable by conditions under which the amino protecting group remains intact. The amino protecting group of the acylating acid P—X'—COOH, if any, thus remains in place for protection of the amino group during the subsequent coupling with the arginine lactam compound to form (c).

The carboxy protecting ester group as used in the specification refers to one of the ester derivatives of the carboxylic acid group commonly employed to block or protect the carboxylic acid group while reactions are carried out on other functional groups on the compound. Examples of such carboxylic acid protecting groups include $C_1$–$C_3$ alkyl, benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2'4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) on other positions of the molecule and can be removed at the appropriate point without disrupting the remainder of the molecule. In particular, it is important not to subject the carboxy-protected molecule to strong nucleophilic bases or reductive conditions employing highly activated metal catalysts such as Raney nickel. (Such harsh removal conditions are also to be avoided when removing amino-protecting groups discussed below.) Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds of Formula I can also be prepared by first synthesizing an Y-Arg dipeptide precursor and then reacting with a protected X-reactant. According to one such method, the cyclic lactam form of arginine (d) is prepared and coupled with an amino protected substituted glycine (g) as shown below to afford the dipeptide (h).

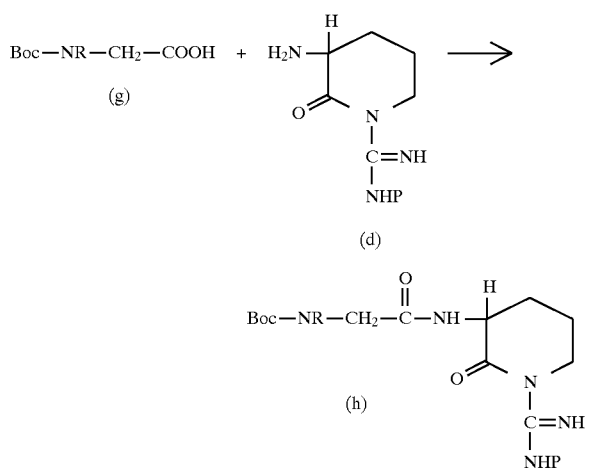

where P represents an amino protecting group such as the benzyloxycarbonyl (Cbz) group, t-butoxycarbonyl (Boc), p-toluenesulfonyl, and the like. Preferably the amino protecting group used is removable by hydrogenation or treatment with mild acid (e.g. trifluoroacetic acid) or a strong acid (e.g. HCl). Examples of other suitable amino protecting groups are provided in "Protective Groups in Organic Synthesis", Second Edition, by T. W. Greene and Peter G. M. Wuts, Chapter 7, page 309–405 (1991), John Wiley & Sons, Inc., publishers, incorporated herein by reference in its entirety. The Boc, or other suitable protecting group, is removed from the glycine nitrogen which is then acylated with the desired amino acid acyl group to afford the tripeptide shown below.

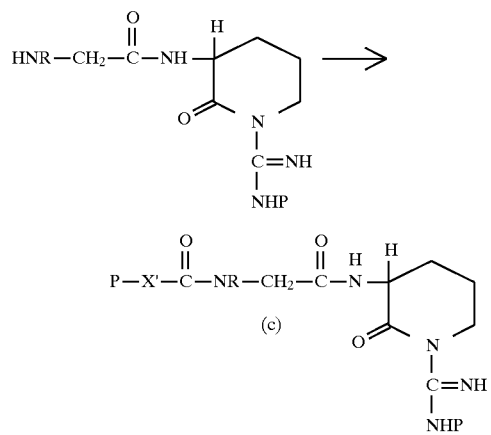

The coupled Arg(P) lactam product (c) is reduced and the protecting groups are removed as described earlier.

The coupling of an P—X'—COOH compound is carried out by first protecting the amino group of the amino acid, if any. Conventional amino protecting groups commonly used for temporary protection or blocking of the amino group are employed. Examples of such protecting groups are described above.

The coupling reactions described above are carried out in the cold preferably at a temperature between about −20° C. and about 15° C. The coupling reactions are carried out in an inert organic solvent such as dimethylformamide, dimethylacetamide, tetrahydrofuran, methylene chloride, chloroform, and like common solvents or a mixture of such solvents. Generally anhydrous conditions are used when, in the coupling reaction, an active ester of the acylating acid is used.

The compounds of the invention are isolated best in the form of acid addition salts. Salts of the compounds of Formula I formed with acids such as those mentioned above are useful as pharmaceutically acceptable salts for administration of the antithrombotic agents and for preparation of formulations of these agents. Other acid addition salts may be prepared and used in the isolation and purification of the peptides. For example, the salts formed with the sulfonic acids such as methanesulfonic acid, n-butanesulfonic acid, p-toluenesulfonic acid and naphthalenesulfonic acid may be so used.

The preferred method for purifying the compounds of Formula I, while at the same time preparing a desired stable salt form, is that described in U.S. Pat. No. 5,250,660. According to the method, stable sulfates or hydrochlorides are provided by preparative purification over $C_{18}$ reversed-phase chromatography in which the aqueous component comprises sulfuric acid or hydrochloric acid at pH 2.5 and acetonitrile as the organic component. The pH of the acidic eluant is adjusted to between about pH 4 and about 6 with an anion exchange resin in the hydroxyl form e.g. Bio-Rad AG-1X8. After adjustment of the pH, the solution of tripeptide sulfate or hydrochloride salt is lyophilized to provide the pure salt in dry powder form. In an example of the process, crude D-hPro-N-(n-propyl)Gly-Arg-H sulfate is dissolved in water and the solution is loaded on Vydac $C_{18}$ RP-HPLC 5 cm×50 cm column. A gradient of 2–10% B (A=0.01% H$_2$SO$_4$; B=acetonitrile) over 10 hours is used. Multiple fractions are collected and those containing product as determined by analytical RP-HPLC are pooled. The pH of the pooled fractions is adjusted to pH 4.0–4.5 with AG-1X8 resin in hydroxide form (Bio-Rad, 3300 Ragatta Blvd., Richmond, Calif. 94804). The solution is filtered and the filtrate is lyophilized to provide the pure D-,(no chiral center), L, tripeptide in the form of the sulfate salt.

The optically active isomers of the diastereomers of the X moiety are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds employed as initial starting materials in the synthesis of the compounds of this invention are well known and, to the extent not commercially available, are readily synthesized by standard procedures commonly employed by those of ordinary skill in the art.

The intermediates for introducing the N-substituted glycine functionality used for making the compounds this invention are made by standard techniques.

For example, a haloacetate ester, such as t-butyl bromoacetate, can be converted into the desired substituted glycine upon treatment with the appropriate primary amine:

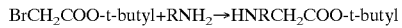

BrCH$_2$COO-t-butyl+RNH$_2$→HNRCH$_2$COO-t-butyl

The t-butyl bromoacetate is allowed to react with the appropriate amine either neat or preferably in a non-reactive solvent, such as an alcohol. It is preferred that a molar excess of the amine is used to force the reaction to completion. Preferably the reaction mixture also contains a non-reactive acid scavenger, such as at least a molar equivalent of triethylamine. While the reactants are usually combined cooled (e.g., 0° C.), the reaction is usually allowed to warm to room temperature after which the reaction is usually complete within 24 hours. Although the bromoacetate is preferred, other haloacetates, such as iodoacetates and chloroacetates, can be employed for this transformation. Other ester groups can similarly be employed. The t-butyl ester is preferred because it can later be easily removed later upon treatment with anisole and trifluoroacetic acid.

A second method for preparing these intermediates is summarized by the following scheme:

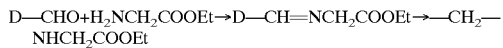

D—CHO+H$_2$NCH$_2$COOEt→D—CH=NCH$_2$COOEt→—CH$_2$—NHCH$_2$COOEt where D—CH$_2$— is an R-group having an unsubstituted methylene group adjacent to the point of attachment to the glycine moiety.

In the above reaction scheme, the appropriate aldehyde is mixed with glycine ester in a non-reactive solvent, such as methanol or ethanol. If a salt form of the glycine ester is used, a molar equivalent of a base, such as potassium hydroxide, can be added to allow generation of the free base of the aminoester. The reaction of the aldehyde and glycine ester formed the intermediate Schiff base which can then be reduced in situ upon treatment with a reducing agent such as sodium cyanoborohydride. Formation of the Schiff base occurs in usually less than an hour; reduction is generally complete after 10–15 hours. The methyl or ethyl esters are particularly useful as these groups can be removed (deblocked) upon treatment withlithium hydroxide in aqueous dioxane. Employing an appropriate ketone instead of aldehyde D—CHO results in the preparation of intermediates wherein the methylene group attached to the glycine amine is substituted.

Alternatively, and especially for those compounds wherein R is Ar (i.e., without an intervening alkyl group), it is preferred to prepare the intermediate P—X'—CONHAr by standard techniques (e.g., reacting an activated form of P—X'—COOH with ArNH$_2$) and then reacting this intermediate with an alkyl haloacetate in the presence of a strong base to give P—X'—CONAr—CH$_2$—COO—alk which can then be further transformed in the usual way.

Many of the final compounds of this invention or intermediates thereto can be interconverted by standard techniques. For example, aryl compounds which are substituted with nitro can be reduced (e.g., in the presence of sodium hydrosulfite in a non-reactive solvent, such as ethanol, water, or a mixture thereof). When the nitro compound is heated at reflux in a water/ethanol mixture in the presence of sodium hydrosulfite, reduction is usually complete within several hours. The resulting amine may be present in the final product; if the amine is present in an intermediate, it may be desirable to convert it to its final desired form (e.g., acylation to provide the acylated amine) or protected to avoid side reactions during the subsequent chemistry. If the free amine is the desired compound, the Cbz protecting group is particularly useful in this regard. Other transformations and intraconversions of this type will be apparent to skilled organic chemists.

The following Examples are provided to further describe the invention and are not to be construed as limitations thereof.

The abbreviations used in the examples have the following meanings.

Amino acids: Arg=arginine, Gly=glycine, hPro=homoproline, Phg=phenylglycine, Phe=phenylalanyl, Sar=sarcosine, Cha=β-cyclohexylalanine, Chg=cyclohexylglycine, 1-Piq=D-cis[4aR,8aR]-1-perhydroisoquinolinecarboxylate, 3-Piq=D-cis[4aR,8aR]-3-perhydroisoquinolinecarboxylate.

Boc=t-butyloxycarbonyl

Bn=benzyl

Cbz=benzyloxycarbonyl

DCC=dicyclohexylcarbodiimide

DMF=dimethylformamide

DMSO=dimethylsulfoxide

EtOAc=ethyl acetate

Et$_2$O=diethyl ether

EtOH=ethanol

FAB-MS=fast atom bombardment mass spectrum

FD-MS=field desorption mass spectrum

HOBT=1-hydroxybenzotriazole hydrate

Ph=phenyl

TFA=trifluoroacetic acid

THF=tetrahydrofuran

TLC=thin layer chromatography

The following parameters for RPHPLC were employed: Solvent A: 0.05% aqueous hydrochloric acid (1.5 mL concentrated hydrochloric acid in 3 L water); Solvent B: acetonitrile; Column: Vydac $C_{18}$-5 cm×25 cm; Flow rate: 10 mL/minute; Method A: 98:2 (A/B), linear ramp to 90:10 (A/B) over 4 hours; Method B: 98:2 (A/B), linear ramp to 80:20 (A/B) over 4 hours; Method C: 98:2 (A/B), linear ramp to 70:30 (A/B) over 4 hours.

Unless otherwise stated, pH adjustments and work up are with aqueous acid or base solutions.

EXAMPLE 1

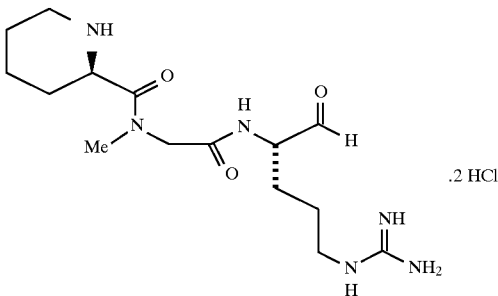

Synthesis of D-hPro-N(Me)Gly-ArgH.2HCl (D-homoprolyl-N-methylglycyl-L-argininal dihydrochloride)

A) Preparation of Cbz-D-hPro-OH.

D-hPro-OH (5.0 g, 38.7 mmol) was dissolved in tetrahydrofuran (100 mL) and water (30 mL). The pH of the solution was adjusted to 9.5 with 2N NaOH and benzyl chloroformate (5.5 ML, 38.7 mmol) was added dropwise and the pH maintained at 9.5 with 2N NaOH. The reaction was stirred for an additional 1 hour at room temperature. The organic solvent was evaporated in vacuo, and diethyl ether (100 mL) and water (50 mL) were added to the residue. The aqueous layer was separated, the pH of the aqueous solution was adjusted to 2.8 with 3N HCl and ethyl acetate (150 mL) was added. The organic layer was separated and dried (MgSO₄) and the filtrate was concentrated in vacuo to give 9.6 g (95%) of a clear oil.

$^1$H NMR

FD-MS, m/e 264 (MH⁺)

B) Preparation of Cbz-D-hPro-N(Me)Gly-OEt

To a stirring solution of Cbz-D-hPro-OH (6.0 g, 22.8 mmol), sarcosine ethyl ester hydrochloride (4.38 g, 28.5 mmol), 1-hydroxybenzotriazole (3.08 g, 22.8 mmol), and N,N-diisopropylethylamine (11.9 mL, 68.4 mmol) in dichloromethane (200 mL) was added 1-(3-dimethylaminopropyl)-3-ethylcarbodiimide hydrochloride (5.46 g, 28.5 mmol). After stirring for 12 hours, the solvent was removed in vacuo and the residue was dissolved in ethyl acetate (500 mL), washed twice with 1N citric acid (200 mL), twice with saturated aqueous NaHCO₃, and twice with a saturated aqueous sodium chloride solution. The organic phase was then dried with MgSO₄, filtered, and concentrated in vacuo. The residue was chromatographed over silica gel, eluting with a step gradient of hexanes through 50% ethyl acetate/hexanes. Fractions containing product (based on TLC) were combined and concentrated to give 6.62 g (80%) of a colorless oil.

$^1$H NMR

FD-MS, m/e 362 (M⁺)

Analysis for $C_{19}H_{26}N_2O_5$: Calc: C, 62.97; H, 7.23; N, 7.73; Found: C, 63.22; H, 7.26; N, 8.00.

C) Preparation of Cbz-D-hPro-N(Me)Gly-OH

To a solution of Cbz-D-hPro-N(Me)Gly-OEt (6 g, 16.6 mmol) in p-dioxane (200 mL) was added a solution of LiOH.H₂O (2.78 g, 66.2 mmol) in water (100 mL) with vigorous stirring. After stirring for 12 hours, the solution was concentrated to a volume of 50 mL, diluted with water (100 mL), and extracted twice with diethyl ether (200 mL). The aqueous phase was adjusted to pH 2 with 5N aqueous HCl and extracted three times with ethyl acetate (150 mL). The combined ethyl acetate extracts were dried with MgSO₄, filtered, and concentrated to give a white solid (5 g, 91%).

$^1$H NMR

FD-MS, m/e 335 (MH₊)

Analysis for $C_{17}H_{22}N_2O_5$: Calc: C, 61.07; H, 6.63; N, 8.38; Found: C, 60.82; H, 6.71; N, 8.17.

D) Preparation of Boc-Arg(Cbz)-OH

Boc-Arg(HCl)-OH (82.1 g, 250 mmol) was dissolved in 5N NaOH (240 mL) in a 3 necked flask. The reaction mixture was chilled to −5° C. and the pH was maintained at 13.2–13.5 using 5N NaOH (250 mL) while adding benzyl chloroformate (143 mL, 1.0 mol) dropwise (55 minutes). The reaction mixture was stirred for an additional 1 hour at −5° C. and diluted with water (100 mL) and diethyl ether (500 mL). The aqueous layer was separated and extracted twice with diethyl ether (500 mL). The aqueous layer was then acidified to pH 3.0 with 3N H₂SO₄ (560 mL) and extracted with ethyl acetate (550 mL). The aqueous layer was separated and extracted once with ethyl acetate. The combined ethyl acetate layers were washed with water, dried (MgSO₄) and concentrated in vacuo to give 66.1 g (65%) of a white solid.

$^1$H NMR

FD-MS 408 (M⁺)

E) Preparation of Boc-Arg(Cbz)-Lactam

Boc-Arg(Cbz)-OH (66.0 g, 0.162 mol) was dissolved in tetrahydrofuran (230 mL) and cooled to −10° C. To this solution was added N-methylmorpholine (18.7 mL, 0.17 mol) followed by isobutyl chloroformate (22.5 mL, 0.17 mol). After stirring 5 minutes at −10° C., triethylamine (23.5 mL, 0.17 mol) was added. After an additional 1 hour at −10° C., the mixture was allowed to warm to room temperature and stirring continued for 1 hour at room temperature. The reaction mixture was then poured into 1 L of ice-water and the resulting precipitate was filtered, washed with cold water, and dried in vacuo. The product was crystallized from ethyl acetate to give 38 g (60%) of a white solid.

$^1$H NMR

FD-MS 391 (MH⁺)

F) Preparation of Arg(Cbz)-Lactam.2HCl

A solution of HCl(g) saturated in ethyl acetate (7.2 L) was added dropwise over 30 minutes to a solution of Boc-Arg (Cbz)-Lactam (641 g, 1.64 mol) dissolved in dichloromethane (3 L) at −10° C. After 1 hour at −10° C. the cold bath was removed and the solution was allowed to warm to room temperature over 3 hours. Diethyl ether (12 L) was added and the resulting precipitate was filtered, washed with diethyl ether, and dried in vacuo to give 580 g (97%).

FD-MS 291 (MH⁺)

G) Preparation of Cbz-D-hPro-N(Me)Gly-Arg(Cbz)lactam

In flask 1, Cbz-D-hPro-N(Me)Gly-OH (4 g, 12 mmol) was dissolved in tetrahydrofuran (50 mL), cooled to −15° C. and N-methylmorpholine (1.3 mL, 12 mmol) was added, followed by isobutyl chloroformate (1.6 mL, 12 mmol). The reaction mixture was allowed to stir at −15° C. for 2 minutes.

In flask 2, Arg(Cbz)-Lactam.2HCl (4.3 g, 12 mmol) was dissolved in dimethylformamide (25 mL), cooled to 0° C., and N,N-diisopropylethylamine (4.2 mL, 24 mmol) was added. The reaction mixture was allowed to stir at 0° C. for 2 minutes.

The contents of flask 2 were added to flask 1 in one portion and the reaction mixture was allowed to stir for 4 hours at −15° C. The cold bath was then removed and the reaction mixture was allowed to slowly warm to room temperature (24 hours). 1N NaHCO$_3$ (5 mL) was added and the solvent was removed in vacuo. The residue was partitioned between ethyl acetate (200 mL) and water (100 mL). The organic layer was separated, and sequentially washed with 1N NaHCO$_3$, water, 1N citric acid, and water. The organic layer was dried (MgSO$_4$), and the filtrate was concentrated in vacuo. The residue was chromatographed over silica gel, eluting with a step gradient of ethyl acetate through 10% tetrahydrofuran/ethyl acetate. The product-containing fractions, as determined by TLC, were combined and concentrated to give 3.8 g (52%) of a white foam.

$^1$H NMR

FD-MS, m/e 607 (MH$^+$)

H) Preparation of D-hPro-N(Me)Gly-ArgH.2HCl

To a stirring solution of Cbz-D-hPro-N(Me)Gly-Arg(Cbz)lactam (3.5 g, 5.8 mmol) in tetrahydrofuran (100 mL) at −23° C., was slowly added a solution of 1N LiAl(O-t-Bu)$_3$H (8.7 mL, 8.7 mmol) in tetrahydrofuran. After 2.5 hours, the reaction mixture was poured into a stirring solution of cold 1N H$_2$SO$_4$ (50 mL). The solution was then diluted with water (200 mL) and washed with hexanes (100 mL). The aqueous phase was then washed three times with 1:1 tetrahydrofuran/hexanes (200 mL), saturated with solid NaCl, and extracted three times with ethyl acetate (150 mL). The combined ethyl acetate extracts were washed with saturated aqueous NaCl (50 mL), dried (MgSO$_4$), and concentrated in vacuo to give 3.1 g of white foam.

The solid was then dissolved in ethanol (200 mL) and water (80 mL) and 1N HCl (20 mL) was added. To this stirring solution was then added 10% Pd-on-carbon (1 g). Hydrogen gas was then bubbled through the solution for 4 hours, and then the reaction was flushed with nitrogen gas and filtered over a pad of Celite®. The ethanol was removed in vacuo at 30° C and then the residue was redissolved in water (50 mL). The pH of the aqueous solution was adjusted to 4 with Bio Rad ion exchange resin (basic form), filtered and lyophilized to give 1.5 g (63%) of a white powder. Purification by RPHPLC was unnecessary.

$^1$H NMR

FAB-MS, m/e 341 (MH$^+$)

Analysis for C$_{15}$H$_{28}$N$_6$O$_3$.2HCl.2H$_2$O: Calc: C, 40.09; H, 7.62; N, 18.70; Found: C, 39.82; H, 7.41; N 18.87.

EXAMPLE 2

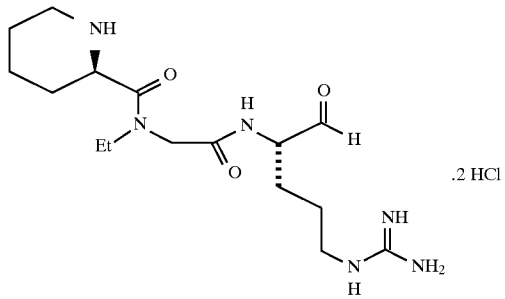

Synthesis of D-hPro-N(Et)Gly-ArgH.2HCl (D-homoprolyl-N-ethylglycyl-L-argininal dihydrochloride)

A) Preparation of N(Et)Gly-O-t-Bu

To a stirring solution of ethylamine (24 mL, 300 mmol) and triethylamine (14 mL, 100 mmol) in ethanol (200 mL) at 0° C., was added via addition funnel a solution of t-butyl bromoacetate (19.5 mL, 100 mmol) in ethanol (50 mL). The cold bath was left unattended and the mixture was allowed to slowly warm to room temperature. After 24 hours, the solvents were removed in vacuo. The residue was dissolved in ethyl acetate, and extracted twice with 1N citric acid. The combined aqueous layers were basified to pH 10 with solid Na$_2$CO$_3$, and then extracted twice with ethyl acetate. The combined ethyl acetate extracts were dried (MgSO$_4$), filtered, and concentrated in vacuo to give 9.8 g (62%) of a yellow oil.

$^1$H NMR

B) Preparation of Cbz-D-hPro-N(Et)-O-t-Bu

By a method substantially equivalent to that described in Example 1-B, 8.6 g (79%) of Cbz-D-hPro-N(n-Et)Gly-O-t-Bu were prepared from Cbz-D-hPro-OH and N(n-Et)Gly-O-t-Bu.

$^1$H NMR

FD-MS, m/e 404 (M$^+$)

Analysis for C$_{22}$H$_{32}$N$_2$O$_5$: Calc: C, 65.32; H, 7.97; N, 6.92; Found: C, 65.60; H, 8.14; N, 7.00.

C) Preparation of Cbz-D-hPro-N(Et)Gly-OH.

To a solution of Cbz-D-hPro-N(Et)Gly-O-t-Bu (5 g, 12.4 mmol) in dichloromethane (50 mL) was added anisole (2.5 mL) and trifluoroacetic acid (50 mL). The mixture was allowed to stir for several hours at room temperature. The solvents were removed in vacuo and the resulting oil was partitioned between saturated aqueous NaHCO$_3$ and diethyl ether. The layers were separated and the organic phase was extracted once with saturated aqueous NaHCO$_3$. The combined aqueous phase was adjusted to pH 2 with 5N aqueous HCl and extracted three times with ethyl acetate (150 mL). The combined ethyl acetate extracts were dried with MgSO$_4$, filtered, and concentrated to give a colorless oil (4.6 g, 106%).

$^1$H NMR

FD-MS, m/e 349 (MH$^+$)

D) Preparation of Cbz-D-hPro-N(Et)Gly-Arg(Cbz)lactam.

By a method substantially equivalent to that described in Example 1-G, 4.9 g (60%) of Cbz-D-hPro-N(Et)Gly-Arg(Cbz)lactam were prepared from Cbz-D-hPro-N(Et)Gly-OH and Arg(Cbz)lactam.2HCl.

$^1$H NMR

FD-MS, m/e 621 (M$^+$)

Analysis for C$_{32}$H$_{40}$N$_6$O$_7$: Calc: C, 61.92; H, 6.50; N, 13.54; Found: C, 61.96; H, 6.59; N, 13.24.

E) Preparation of D-hPro-N(Et)Gly-ArgH.2HCl

By a method substantially equivalent to that described in Example 1-H, 2 g (83%) of crude D-hPro-N(Et)Gly-ArgH.2HCl were prepared. This material was purified by RPHPLC method B to give 0.18 g (9%) of pure product.

$^1$H NMR

FAB-MS, m/e 355 (MH$^+$)

Analysis for C$_{16}$H$_{30}$N$_6$O$_3$.2HCl: Calc: C, 44.96; H, 7.54; N, 19.66; Found: C, 44.80; H, 7.52; N 19.36.

EXAMPLE 3

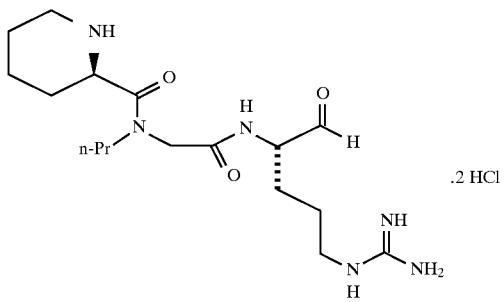

Synthesis of D-hPro-N(n-Pr)Gly-ArgH.2HCl (D-homoprolyl-N-n-propylglycyl-L-argininal dihydrochloride)

A) Preparation of N(n-Pr)Gly-O-t-Bu

By a method substantially equivalent to that described in Example 2-A, 13.1 g (76%) of N(n-Pr)Gly-O-t-Bu were prepared from t-butyl bromoacetate and n-propylamine.

$^1$H NMR

B) Preparation of Cbz-D-hPro-N(n-Pr)Gly-O-t-Bu

By a method substantially equivalent to that described in Example 1-B, 9.4 g (83%) of Cbz-D-hPro-N(n-Pr)Gly-O-t-Bu were prepared from Cbz-D-hPro-OH and N(n-Pr)Gly-O-t-Bu.

$^1$H NMR

FD-MS, m/e 418 (M$^+$)

C) Preparation of Cbz-D-hPro-N(n-Pr)Gly-OH

By a method substantially equivalent to that described in Example 2-C, 7.3 g (90%) of Cbz-D-hPro-N(n-Pr)Gly-OH were prepared.

$^1$H NMR

FD-MS, m/e 363 (MH$^+$)

D) Preparation of Cbz-D-hPro-N(n-Pr)Gly-Arg(Cbz)lactam

By a method substantially equivalent to that described in Example 1-G, 3.8 g (43%) of Cbz-D-hPro-N(n-Pr)Gly-Arg(Cbz)lactam were prepared from Cbz-D-hPro-N(n-Pr)Gly-OH and Arg(Cbz)lactam.2HCl.

$^1$H NMR

FD-MS, m/e 635 (M$^+$)

Analysis for $C_{33}H_{42}N_6O_7$: Calc: C, 62.45; H, 6.67; N, 13.24; Found: C, 62.23; H, 6.77; N, 13.02.

E) Preparation of D-hPro-N(n-Pr)Gly-ArgH.2HCl

By a method substantially equivalent to that described in Example 1-H, 1.4 g (81%) of crude D-hPro-N(n-Pr)Gly-ArgH.2HCl were prepared. 1 g of this material was purified by RPHPLC method B to give 0.37 g (37%) of pure D-hPro-N(n-Pr)Gly-ArgH.2HCl.

$^1$H NMR

FAB-MS, m/e 369 (MH$^+$)

Analysis for $C_{17}H_{32}N_6O_3$.2HCl: Calc: C, 46.26; H, 7.76; N, 19.04; Found: C, 46.42; H, 7.61; N, 18.76.

EXAMPLE 4

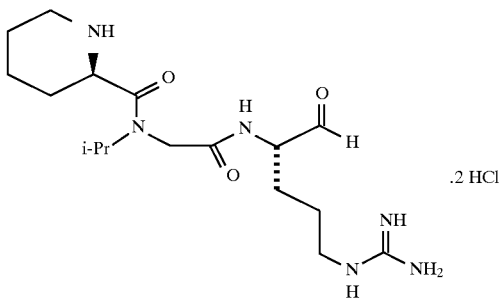

Synthesis of D-hPro-N(i-Pr)Gly-ArgH.2HCl

A) Preparation of N-(i-Pr)Gly-O-t-Bu

By a method substantially equivalent to that described in Example 2-A, 12.1 g (70%) of N(i-Pr)Gly-O-t-Bu were prepared from t-butyl bromoacetate and isopropylamine.

$^1$H NMR

B) Preparation of Cbz-D-hPro-N(i-Pr)Gly-O-t-Bu

By a method substantially equivalent to that described in Example 1-B, 3.3 g (29%) of Cbz-D-hPro-N(i-Pr)Gly-O-t-Bu were prepared from Cbz-D-hPro-OH and N(i-Pr)Gly-O-t-t-Bu.

$^1$H NMR

FD-MS, m/e 418 (M$^+$)

C) Preparation of Cbz-D-hPro-N(i-Pr)Gly-OH

By a method substantially equivalent to that described in Example 2-C, 1.5 g (52%) of Cbz-D-hPro-N(i-Pr)Gly-OH were prepared.

$^1$H NMR

FD-MS, m/e 363 (MH$^+$)

D) Preparation of Cbz-D-hPro-N(i-Pr)Gly-Arg(Cbz)lactam

By a method substantially equivalent to that described in Example 1-G, 0.34 g (13%) of Cbz-D-hPro-N(i-Pr)Gly-Arg(Cbz)lactam were prepared from Cbz-D-hPro-N(i-Pr)Gly-OH and Arg(Cbz)lactam.2HCl.

$^1$H NMR

FD-MS, m/e 635 (M$^+$)

Analysis for $C_{33}H_{42}N_6O_7$; Calc: C, 62.45; H, 6.67; N, 13.24; Found: C, 62.69; H, 6.78; N, 13.27.

E) Preparation of D-hPro-N(i-Pr)Gly-ArgH.2HCl

By a method substantially equivalent to that described in Example 1-H, 0.21 g (99%) of D-hPro-N(i-Pr)Gly-ArgH.2HCl were prepared. Purification by RPHPLC was unnecessary.

$^1$H NMR

FD-MS, m/e 369 (M$^+$)

Analysis for $C_{17}H_{32}N_6O_3$.3HCl.2H$_2$O: Calc: C, 39.73; H, 7.65; N, 16.35; Found: C, 40.19; H, 7.50; N, 16.11.

EXAMPLE 5

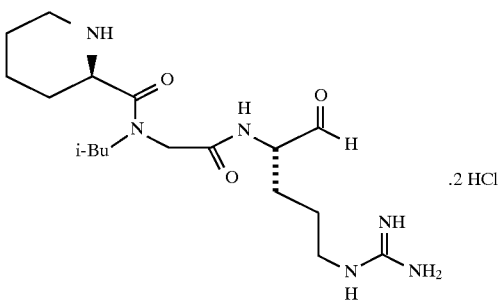

Synthesis of D-hPro-N(i-BU)Gly-ArgH.2HCl

A) Preparation of N(i-Bu)Gly-O-t-Bu

By a method substantially equivalent to that described in Example 2-A, 19 g (58%) of N(i-Bu)Gly-O-t-Bu were prepared from t-butyl bromoacetate and isobutylamine.

$^1$H NMR

B) Preparation of Cbz-D-hPro-N(i-Bu)Gly-O-t-Bu.

By a method substantially equivalent to that described in Example 1-B, 8.1 g (47%) of Cbz-D-hPro-N(i-Bu)Gly-O-t-Bu were prepared from Cbz-D-hPro-OH and N(i-Bu)Gly-O-t-Bu.

$^1$H NMR

FD-MS, m/e 432 (M$^+$)

Analysis for $C_{24}H_{36}N_2O_5$: Calc: C, 66.64; H, 8.39; N, 6.48; Found: C, 66.86; H, 8.19; N, 6.39.

C) Preparation of Cbz-D-hPro-N(i-Bu)Gly-OH

By a method substantially equivalent to that described in Example 2-C, 6.6 g (100%) of Cbz-D-hPro-N(i-Bu)Gly-OH were prepared.

$^1$H NMR

FD-MS, m/e 377 (MH$^+$)

Analysis for $C_{20}H_{28}N_2O_5$: Calc: C, 63.81; H, 7.50; N, 7.44; Found: C, 63.56; H, 7.60; N, 7.34.

D) Preparation of Cbz-D-hPro-N(i-Bu)Gly-Arg(Cbz) lactam.

By a method substantially equivalent to that described in Example 1-G, 3.5 g (54%) of Cbz-D-hPro-N(i-Bu)Gly-Arg(Cbz)lactam were prepared from Cbz-D-hPro-N(i-Bu)Gly-OH and Arg(Cbz)lactam.2HCl.

$^1$H NMR

FD-MS, m/e 649 (M$^+$)

Analysis for $C_{34}H_{44}N_6O_7$: Calc: C, 62.95; H, 6.84; N, 12.95; Found: C, 63.11; H, 7.06; N, 13.07.

E) Preparation of D-hPro-N(i-Bu)Gly-ArgH.2HCl

To a stirring solution of Cbz-D-hPro-N(i-Bu)Gly-Arg(Cbz)lactam (3 g, 4.6 mmol) in anhydrous tetrahydrofuran (100 mL) at −78° C. was added via syringe a solution of lithium aluminum hydride 1N in tetrahydrofuran (4.6 mL, 4.6 mmol) over 5 minutes. After 30 minutes, the reaction mixture was poured into a solution of cold, 0.5N $H_2SO_4$ (100 mL). The solution was then diluted with water (100 mL) and washed with hexanes (100 mL). The aqueous phase was then washed three times with 1:1 tetrahydrofuran/hexanes (200 mL), saturated with solid NaCl, and extracted four times with ethyl acetate (150 mL). The combined ethyl acetate extracts were washed with saturated aqueous NaCl (50 mL), dried (MgSO$_4$), and concentrated in vacuo to give a white foam.

The foam was then dissolved in ethanol (200 mL) and water (100 mL) and 1N HCl (9 mL) were added. To this stirring solution was then added 5% Pd-on-carbon (2.5 g). Hydrogen gas was then bubbled through the solution for 4 hours, and then the reaction was flushed with nitrogen gas and filtered over a pad of Celite®. The ethanol was removed in vacuo at 30° C. and then the residue was redissolved in water (50 mL). The pH of the aqueous solution was adjusted to 4 with Bio Rad ion exchange resin (basic form), filtered and lyophilized to give 1.9 g (89%) of crude D-hPro-N(i-Bu)Gly-ArgH.2HCl. 1.2 g of this material were purified by RPHPLC method C to give 0.29 g (24%) of pure D-hPro-N(i-Bu)Gly-ArgH.2HCl.

$^1$H NMR

FD-MS, m/e 383 (MH$^+$)

Analysis for $C_{18}H_{34}N_6O_3$.3HCl.H$_2$O:

EXAMPLE 6

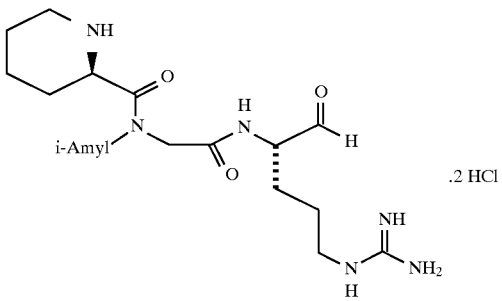

Synthesis of D-hPro-N(isoamyl)Gly-ArgH.2HCl

A) Preparation of N(isoamyl)Gly-O-t-Bu

By a method substantially equivalent to that described in Example 2-A, 16.6 g (82%) of N(isoamyl)Gly-O-t-Bu were prepared from t-butyl bromoacetate and isoamylamine.

$^1$H NMR

B) Preparation of Cbz-D-hPro-N(isoamyl)Gly-O-t-Bu

By a method substantially equivalent to that described in Example 1-B, 8.7 g (72%) of Cbz-D-hPro-N(isoamyl)Gly-O-t-Bu were prepared from Cbz-D-hPro-OH and N(isoamyl)Gly-O-t-Bu.

$^1$H NMR

FD-MS, m/e 446 (M$^+$)

Analysis for $C_{25}H_{38}N_2O_5$: Calc: C, 67.24; H, 8.58; N, 6.27; Found: C, 67.50; H, 8.72; N, 6.42.

C) Preparation of Cbz-D-hPro-N(isoamyl)Gly-OH

By a method substantially equivalent to that described in Example 2-C, 4.8 g (109%) of Cbz-D-hPro-N(isoamyl)Gly-OH were prepared.

$^1$H NMR

FD-MS, m/e 391 (MH$^+$)

D) Preparation of Cbz-D-hPro-N(isoamyl)Gly-Arg(Cbz) lactam

By a method substantially equivalent to that described in Example 1-G, 4 g (61%) of Cbz-D-hPro-N(isoamyl)Gly-Arg(Cbz)lactam were prepared from Cbz-D-hPro-N(isoamyl)Gly-OH and Arg(Cbz)lactam.2HCl.

$^1$H NMR

FD-MS, m/e 663 (M$^+$)

Analysis for $C_{35}H_{46}N_6O_7$: Calc: C, 63.43; H. 7.00; N, 12.68; Found: C, 63.72; H, 7.14; N, 12.43.

E) Preparation of D-hPro-N(isoamyl)Gly-ArgH.2HCl.

By a method substantially equivalent to that described in Example 1-H, 2.4 g (67%) of D-hPro-N(isoamyl)Gly-ArgH.2HCl were prepared. RPHPLC purification was unnecessary.

$^1$H NMR

FD-MS, m/e 397 (MH$^+$)

Analysis for $C_{19}H_{36}N_6O_3$.2HCl.H$_2$O: Calc: C, 46.43; H, 8.28; N, 17.12; Found: C, 46.82; H, 8.27; N, 17.24.

EXAMPLE 7

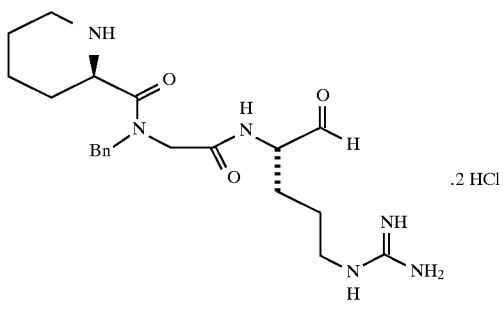

Synthesis of D-hPro-N(Bn)Gly-ArgH.2HCl

A) Preparation of Cbz-D-hPro-N(Bn)Gly-OEt

By a method substantially equivalent to that described in Example 1-B, 5.3 g (30%) of Cbz-D-hPro-N(Bn)Gly-OEt were prepared from Cbz-D-hPro-OH and N(Bn)Gly-OEt.

$^1$H NMR

FD-MS, m/e 438 (M$^+$)

Analysis for $C_{25}H_{30}N_2O_5$: Calc: C, 68.47; H, 6.90; N, 6.39; Found: C, 68.22; H, 6.90; N, 6.36.

B) Preparation of Cbz-D-hPro-N(Bn)Gly-OH

By a method substantially equivalent to that described in Example 1-C, 4.6 g (98%) of Cbz-D-hPro-N(Bn)Gly-OH were prepared.

$^1$H NMR

FD-MS, m/e 411 (MH$^+$)

Analysis for $C_{23}H_{26}N_2O_5$: Calc: C, 67.30; H, 6.38; N 6.82; Found: C, 67.43; H, 6.40; N 6.87.

C) Preparation of Cbz-D-hPro-N(Bn)Gly-Arg(Cbz)lactam

By a method substantially equivalent to that described in Example 1-G, 5.5 g (81%) of Cbz-D-hPro-N(Bn)Gly-Arg(Cbz)lactam were prepared from Cbz-D-hPro-N(Bn)Gly-OH and Arg(Cbz)lactam.2HCl.

$^1$H NMR

FD-MS, m/e 683 (M$^+$)

Analysis for $C_{37}H_{42}N_6O_7$: Calc: C, 65.09; H, 6.20; N, 12.31; Found: C, 65.38; H, 6.44; N, 12.25.

D) Preparation of D-hPro-N(Bn)Gly-ArgH.2HCl

By a method substantially equivalent to that described in Example 5-E, 2.3 g (80%) of D-hPro-N(Bn)Gly-ArgH.2HCl were prepared. Purification by RPHPLC was unnecessary.

$^1$H NMR

FAB-MS, m/e 417 (MH$^+$)

Analysis for $C_{21}H_{32}N_6O_3$.3HCl.0.5H$_2$O: Calc: C, 47.15; H, 6.78; N, 15.71; Found: C, 46.89; H, 6.67; N, 16.05.

EXAMPLE 8

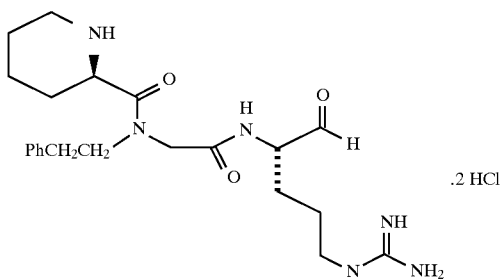

Synthesis of D-hPro-N(PhCH$_2$CH$_2$)Gly-ArgH.2HCl (D-homoprolyl-N-(2-phenylethyl)glycyl-L-argininal dihydrochloride)

A) Preparation of N(PhCH$_2$CH$_2$)Gly-O-t-Bu

By a method substantially equivalent to that described in Example 2-A, 10.8 g (56%) of N(PhCH$_2$CH$_2$)Gly-O-t-Bu were prepared from t-butyl bromoacetate and phenethylamine.

$^1$H NMR

B) Preparation of Cbz-D-hPro-N(PhCH$_2$CH$_2$)Gly-O-t-Bu

By a method substantially equivalent to that described in Example 1-B, 10.8 g (56%) of Cbz-D-hPro-N(PhCH$_2$CH$_2$)Gly-O-t-Bu were prepared from Cbz-D-hPro-OH and N(PhCH$_2$CH$_2$)Gly-O-t-Bu.

$^1$H NMR

FD-MS, m/e 480 (M$^+$)

Analysis for $C_{28}H_{36}N_2O_5$; Calc: C, 69.98; H, 7.55; N, 5.83; Found: C, 69.68; H, 7.56; N, 5.77.

C) Preparation of Cbz-D-hPro-N(PhCH$_2$CH$_2$)Gly-OH

By a method substantially equivalent to that described in Example 2-C, 9.2 g (100%) of Cbz-D-hPro-N(PhCH$_2$CH$_2$)Gly-OH were prepared.

$^1$H NMR

FD-MS, m/e 425 (MH$^+$)

Analysis for $C_{24}H_{28}N_2O_5$; Calc: C, 67.91; H, 6.65; N, 6.60; Found: C, 68.19; H, 6.68; N, 6.71.

D) Preparation of Cbz-D-hPro-N(PhCH$_2$CH$_2$)Gly-Arg(Cbz)lactam

By a method substantially equivalent to that described in Example 1-G, 4.4 g (53%) of Cbz-D-hPro-N(PhCH$_2$CH$_2$)Gly-Arg(Cbz)lactam were prepared from Cbz-D-hPro-N(PhCH$_2$CH$_2$)Gly-OH and Arg(Cbz)lactam.2HCl.

$^1$H NMR

FD-MS, m/e 698 (MH$^+$)

Analysis Calculated for $C_{38}H_{44}N_6O_7$; Calc: C, 65.50; H, 6.37; N, 12.06; Found: C, 65.52; H, 6.58; N. 11.85.

E) Preparation of D-hPro-N(PhCH$_2$CH$_2$)Gly-ArgH.2HCl

By a method substantially equivalent to that described in Example 5-E, 2.2 g (87%) of D-hPro-N(PhCH$_2$CH$_2$)Gly-ArgH.2HCl were prepared. Purification by RPHPLC was unnecessary.

$^1$H NMR

FAB-MS, m/e 431 (MH$^+$)

Analysis for $C_{22}H_{34}N_6O_3$.2HCl: Calc: C, 52.48; H, 7.21; N, 16.69; Found: C, 52.22; H, 7.03; N, 16.43.

EXAMPLE 9

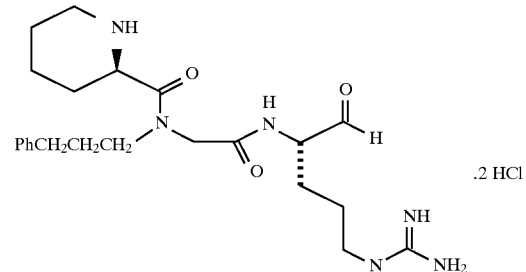

Synthesis of D-hPro-N(PhCH$_2$CH$_2$CH$_2$)Gly-ArgH.2HCl

A) Preparation of N(PhCH$_2$CH$_2$CH$_2$)Gly-OMe

To a stirring suspension of glycine methyl ester hydrochloride (62.8 g, 500 mmol) in anhydrous methanol (500 mL) was added KOH (28.1 g, 500 mmol) and 3 Å molecular sieves (approx. 200 g). After stirring for 30 minutes the KOH completely dissolved. An addition funnel was then added and charged with a solution of 3-phenylpropionaldehyde (13.4 g, 100 mmol) in methanol (50 mL). This solution was then added dropwise over 30 minutes. NaBH$_3$CN (6.3 g, 100 mmol) was added in portions and the reaction was allowed to stir for 16 hours under nitrogen. The mixture was filtered and the filtrate was concentrated in vacuo. The residue was dissolved in ethyl acetate, and extracted twice with 1N HCl. The combined aqueous layers were basified to pH 10 with solid N$_2$CO$_3$ and then extracted twice with ethyl acetate. The combined ethyl acetate extracts were dried (MgSO$_4$), filtered, and concentrated in vacuo to give 4.3 g (22%) of a yellow syrup.

$^1$H NMR

B) Preparation of Cbz-D-hPro-N(PhCH$_2$CH$_2$CH$_2$)Gly-OMe

By a method substantially equivalent to that described in Example 1-B, 4.3 g (22%) of Cbz-D-hPro-N (PhCH$_2$CH$_2$CH$_2$)Gly-OMe were prepared from Cbz-D-hPro-OH and N(PhCH$_2$CH$_2$CH$_2$)Gly-OMe.

$^1$H NMR

FD-MS, m/e 453 (M$^+$)

Analysis for C$_{26}$H$_{32}$N$_2$O$_5$: Calc: C, 69.01; H, 7.13; N, 6.19; Found: C, 68.62; H, 6.76; N, 7.62.

C) Preparation of Cbz-D-hPro-N(PhCH$_2$CH$_2$CH$_2$)Gly-OH

By a method substantially equivalent to that described in Example 1-C, 3.6 g (88%) of Cbz-D-hPro-N (PhCH$_2$CH$_2$CH$_2$)Gly-OH were prepared.

$^1$H NMR

FD-MS, m/e 439 (M$^+$)

Analysis for C$_{25}$H$_{30}$N$_2$O$_5$: Calc: C, 68.47; H, 6.90; N, 6.39; Found: C, 68.19; H, 6.71; N, 6.65.

D) Preparation of Cbz-D-hPro-N(PhCH$_2$CH$_2$CH$_2$)Gly-Arg(Cbz)lactam

By a method substantially equivalent to that described in Example 1-G, 3.3 g (68%) of Cbz-D-hPro-N (PhCH$_2$CH$_2$CH$_2$)Gly-Arg(Cbz)lactam were prepared from Cbz-D-hPro-N(PhCH$_2$CH$_2$CH$_2$)Gly-OH and Arg(Cbz) lactam.2HCl.

$^1$H NMR

FD-MS, m/e 711 (M$^+$)

Analysis for C$_{39}$H$_{46}$N$_6$O$_7$; Calc: C, 65.90; H, 6.52; N, 11.82; Found: C, 65.77; H, 6.54; N, 12.09.

E) Preparation of D-hPro-N(PhCH$_2$CH$_2$CH$_2$)Gly-ArgH.2HCl

By a method substantially equivalent to that described in Example 5-E, 1.8 g (89%) of crude D-hPro-N (PhCH$_2$CH$_2$CH$_2$)Gly-ArgH.2HCl were prepared. 1.2 g of this material were purified by RPHPLC method C to give 0.76 g (63%) of pure D-hPro-N(PhCH$_2$CH$_2$CH$_2$)Gly-ArgH.2HCl.

$^1$H NMR

FAB-MS, m/e 445 (MH$^+$)

Analysis for C$_{23}$H$_{36}$N$_6$O$_3$.2HCl Calc: C, 53.38; H, 7.40; N, 16.24; Found: C 53.67; H, 7.19; N, 16.34.

EXAMPLE 10

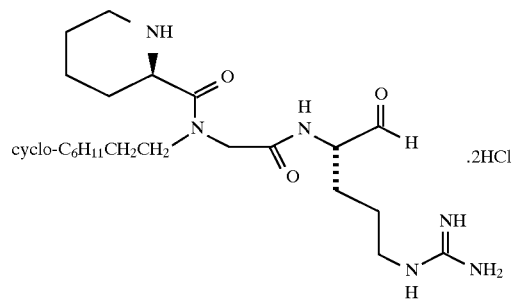

Synthesis of D-hPro-N(cyclohexyl-CH$_2$CH$_2$)Gly-ArgH.2HCl

A) Preparation of N(cyclohexyl-CH$_2$CH$_2$)Gly-OMe

By a method substantially equivalent to that described in Example 9-A, 8 g (71%) of N(cyclohexyl-CH$_2$CH$_2$)Gly-OMe were prepared from Gly-OMe.HCl and cyclohexylacetaldehyde.

$^1$H NMR

B) Preparation of Cbz-D-hPro-N(cyclohexyl-CH$_2$CH$_2$)Gly-OMe

By a method substantially equivalent to that described in Example 1-B, 7.9 g (71%) of Cbz-D-hPro-N(cyclohexyl-CH$_2$CH$_2$)Gly-OMe were prepared from Cbz-D-hPro-OH and N(cyclohexyl-CH$_2$CH$_2$)Gly-OMe.

$^1$H NMR

FD-MS, m/e 444 (M$^+$)

Analysis for C$_{25}$H$_{36}$N$_2$O$_5$: Calc: C, 67.54; H, 8.16; N, 6.30; Found: C, 67.82; H, 8.07; N, 6.54.

C) Preparation of Cbz-D-hPro-N(cyclohexyl-CH$_2$CH$_2$)Gly-OH

By a method substantially equivalent to that described in Example 1-C, 6.4 g (94%) of Cbz-D-hPro-N(cyclohexyl-CH$_2$CH$_2$)Gly-OH were prepared.

$^1$H NMR

FD-MS, m/e 431 (MH$^+$)

Analysis for C$_{24}$H$_{34}$N$_2$O$_5$: Calc: C, 66.95; H, 7.96; N, 6.50; Found: C, 67.16; H, 8.20; N, 6.54.

D) Preparation of Cbz-D-hPro-N(cyclohexyl-CH$_2$CH$_2$)Gly-Arg(Cbz)lactam

By a method substantially equivalent to that described in Example 1-G, 3.9 g (78%) of Cbz-D-hPro-N(cyclohexyl-CH$_2$CH$_2$)Gly-Arg(Cbz)lactam were prepared from Cbz-D-hPro-N(cyclohexyl-CH$_2$CH$_2$)Gly-OH and Arg(Cbz) lactam.2HCl.

$^1$H NMR

FD-MS, m/e 703 (M$^+$)

Analysis for C$_{38}$H$_{50}$N$_6$O$_7$; Calc: C, 64.94; H, 7.17; N, 11.96; Found: C, 64.65; H, 7.37; N, 11.78.

E) Preparation of D-hPro-N(cyclohexyl-CH$_2$CH$_2$)Gly-ArgH.2HCl

By a method substantially equivalent to that described in Example 5-E, 1.5 g (68%) of D-hPro-N(cyclohexyl-CH$_2$CH$_2$)Gly-ArgH.2HCl were prepared. 1.2 g of this material were purified by RPHPLC method C to give 0.38 g (32%) of pure D-hPro-N(cyclohexyl-CH$_2$CH$_2$)Gly-ArgH.2HCl.

$^1$H NMR

FAB-MS, m/e 437 (MH$^+$)

Analysis for C$_{22}$H$_{40}$N$_6$O$_3$.2HCl: Calc: C, 51.86; H, 8.31; N, 16.49; Found: C, 51.99; H, 8.18; N, 16.80.

EXAMPLE 11

Synthesis of D-hPro-N(Ph)Gly-ArgH.2HCl

A) Preparation of Cbz-D-hPro-NHC$_6$H$_5$

By a method substantially equivalent to that described in Example 1-B, 10.8 g (93%) of Cbz-D-hPro-NHC$_6$H$_5$ were prepared from Cbz-D-hPro-OH and aniline.

$^1$H NMR

FD-MS, m/e 338 (M$^+$)

Analysis for C$_{20}$H$_{22}$N$_2$O$_3$: Calc: C, 70.99; H, 6.55; N, 8.28; Found: C, 70.73; H, 6.58; N, 8.11.

B) Preparation of Cbz-D-hPro-N(Ph)Gly-OEt

To a solution of Cbz-D-hPro-NHC$_6$H$_5$ (7.7 g, 22.8 mmol) in tetrahydrofuran (300 mL) was added ethyl bromoacetate (12.6 mL, 113.8 mmol). The solution was cooled to 0° C. and NaH 60% suspension (2 g, 50 mmol) was added in small portions over 20 minutes, with gas evolution. After gas evolution had ceased, the cold bath was left unattended and the mixture was allowed to warm slowly to room temperature. After 18 hours, 1N citric acid (50 mL) was added slowly with cooling. The mixture was partitioned between ethyl acetate (300 mL) and 1N citric acid (300 mL). The organic layer was washed twice with 1N citric acid (200 mL), twice with saturated aqueous NaHCO$_3$, and twice with saturated aqueous sodium chloride solution. The ethyl acetate layer was dried (MgSO$_4$), filtered and concentrated in vacuo. The residue was chromatographed over silica gel, eluting with a step gradient of hexanes through 50% ethyl acetate/hexanes. Fractions containing product (as judged by TLC) were combined and concentrated in vacuo to give a yellow oil (9.2 g, 96%).

$^1$H NMR

FD-MS, m/e 424 (M$^+$)

Analysis for C$_{24}$H$_{28}$N$_2$O$_5$: Calc: C, 67.91; H, 6.65; N, 6.60; Found: C, 68.18; H, 6.95; N, 6.63.

C) Preparation of Cbz-D-hPro-N(Ph)Gly-OH

By a method substantially equivalent to that described in Example 1-C, 7.1 g (95%) of Cbz-D-hPro-N(Ph)Gly-OH were prepared.

$^1$H NMR

FD-MS, m/e 397 (MH$^+$)

Analysis for C$_{22}$H$_{24}$N$_2$O$_5$: Calc: C, 66.65; H, 6.10; N, 7.07; Found: C, 66.31; H, 5.88; N, 7.13.

D) Preparation of Cbz-D-hPro-N(Ph)Gly-Arg(Cbz)lactam

By a method substantially equivalent to that described in Example 1-G, 6.9 g (68%) of Cbz-D-hPro-N(Ph)Gly-Arg(Cbz)lactam were prepared from Cbz-D-hPro-N(Ph)Gly-OH and Arg(Cbz)lactam.2HCl.

$^1$H NMR

FD-MS, m/e 669 (M$^+$)

Analysis for C$_{36}$H$_{40}$N$_6$O$_7$: Calc: C, 64.66; H, 6.03; N, 12.57; Found: C, 64.60; H, 6.10; N, 12.38.

E) Preparation of D-hPro-N(Ph)Gly-ArgH.2HCl

By a method substantially equivalent to that described in Example 1-H, 2.2 g (63%) of D-hPro-N(Ph)Gly-ArgH.2HCl were prepared. RPHPLC purification was unnecessary.

$^1$H NMR

FAB-MS, m/e 404 (MH$^+$)

Analysis for C$_{20}$H$_{30}$N$_6$O$_3$.2HCl.1.5H$_2$O: Calc: C, 47.81; H, 7.02; N, 16.73; Found: C, 47.89; H, 6.87; N, 16.63.

EXAMPLE 12

Synthesis of D-hPro-N(o-Me-Ph)Gly-ArgH.2HCl

A) Preparation of Cbz-D-hPro-NH(o-Me-Ph)

By a method substantially equivalent to that described in Example 1-B, 9.8 g (105%) of Cbz-D-hPro-NH(o-Me-Ph) were prepared from Cbz-D-hPro-OH and o-methylaniline.

$^1$H NMR

FD-MS, m/e 352 (M$^+$)

Analysis for C$_{21}$H$_{24}$N$_2$O$_3$.0.1EtOAc: Calc: C, 71.15; H, 6.92. N, 7.75; Found: C, 71.33; H, 6.96. N, 8.00.

B) Preparation of Cbz-D-hPro-N(o-Me-Ph)Gly-OEt

By a method substantially equivalent to that described in Example 11-B, 8.0 g (93%) of Cbz-D-hPro-N(o-Me-Ph)Gly-OEt were prepared.

$^1$H NMR

FD-MS, m/e 438 (M$^+$)

Analysis for C$_{25}$H$_{30}$N$_2$O$_5$: Calc: C, 68.47; H, 6.90; N, 6.39; Found: C, 68.37; H, 6.97; N, 6.45.

C) Preparation of Cbz-D-hPro-N(o-Me-Ph)Gly-OH

By a method substantially equivalent to that described in Example 1-C, 6.5 g (83%) of Cbz-D-hPro-N(o-Me-Ph)Gly-OH were prepared.

$^1$H NMR

FD-MS, m/e 411 (M$^+$)

D) Preparation of Cbz-D-hPro-N(o-Me-Ph)Gly-Arg(Cbz)lactam

By a method substantially equivalent to that described in Example 1-G, 5.7 g (63%) of Cbz-D-hPro-N(o-Me-Ph)Gly-Arg(Cbz)lactam were prepared from Cbz-D-hPro-N(o-Me-Ph)Gly-OH and Arg(Cbz)lactam.2HCl.

$^1$H NMR

FD-MS, m/e 683 (M$^+$)

Analysis for C$_{37}$H$_{42}$N$_6$O$_7$: Calc: C, 65.09; H, 6.20; N 12.31; Found: C, 64.82; H, 6.31; N, 12.10.

E) Preparation of D-hPro-N(o-Me-Ph)Gly-ArgH.2HCl

By a method substantially equivalent to that described in Example 1-H, 0.66 g (47%) of D-hPro-N(o-Me-Ph)Gly-ArgH.2HCl were prepared. RPHPLC purification was unnecessary.

$^1$H NMR

FAB-MS, m/e 417 (MH$^+$)

Analysis for C$_{21}$H$_{32}$N$_6$O$_3$.2HCl .H$_2$O: Calc: C, 50.60; H, 7.08; N 16.86; Found: C, 50.30; H, 7.65; N, 16.82.

EXAMPLE 13

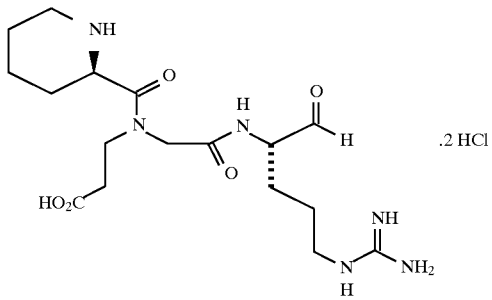

Synthesis of D-hPro-N(CH$_2$CH$_2$COOH)Gly-ArgH.2HCl

A) Preparation of N(CH$_2$CH$_2$COOBn)Gly-O-t-Bu

To a solution of glycine t-butyl ester hydrochloride (20.7 g, 123 mmol) in DMF (50 mL) was added DIEA (21.5 mL, 123 mmol) and benzyl acrylate (20 g, 123 mmol). The mixture was allowed to stir at room temperature for 4 hours. This solution was concentrated in vacuo and the residue partitioned between saturated aqueous NaHCO$_3$ and ethyl acetate and separated. The organic layer was washed once with saturated aqueous NaHCO$_3$ and twice with brine. The ethyl acetate layer was dried (MgSO$_4$), filtered and concentrated in vacuo to give 30 g (83%) of a slightly amber oil.

$^1$H NMR

B) Preparation of Cbz-D-hPro-N(CH$_2$CH$_2$COOBn)Gly-O-t-Bu

By a method substantially equivalent to that described in Example 1-B, 4 g (20%) of Cbz-D-hPro-N(CH$_2$CH$_2$COOBn)Gly-O-t-Bu were prepared from Cbz-D-hPro-OH and N(CH$_2$CH$_2$COOBn)Gly-O-t-Bu.

$^1$H NMR

FD-MS, m/e 538 (M$^+$)

Analysis for C$_{30}$H$_{38}$N$_2$O$_7$: Calc: C, 66.90; H, 7.11. N, 5.21; Found: C, 67.09; H, 6.99. N, 5.24.

C) Preparation of Cbz-D-hPro-N(CH$_2$CH$_2$COOBn)Gly-OH

By a method substantially equivalent to that described in Example 2-C, 3.75 g (100%) of Cbz-D-hPro-N(CH$_2$CH$_2$COOBn)Gly-OH were prepared.

$^1$H NMR

FD-MS, m/e 483 (M$^+$)

D) Preparation of Cbz-D-hPro-N(CH$_2$CH$_2$COOBn)Gly-Arg(Cbz)lactam

By a method substantially equivalent to that described in Example 1-G, 2.92 g (52%) of Cbz-D-hPro-N(CH$_2$CH$_2$COOBn)Gly-Arg(Cbz)lactam were prepared from Cbz-D-hPro-N(CH$_2$CH$_2$COOBn)Gly-OH and Arg(Cbz)lactam.2HCl.

$^1$H NMR

FD-MS, m/e 756 (MH$^+$)

E) Preparation of D-hPro-N(CH$_2$CH$_2$COOH)Gly-ArgH.2HCl

By a method substantially equivalent to that described in Example 5-E, 1.44 g (85%) of D-hPro-N(CH$_2$CH$_2$COOH)Gly-ArgH.2HCl were prepared. One gram of this material was purified by RPHPLC method B to give 0.19 g (19%) of pure product.

$^1$H NMR

FD-MS, 399 m/e (M$^+$)

Analysis for C$_{17}$H$_{30}$N$_6$O$_5$.2HCl.0.5H$_2$O: Calc: C, 42.50; H, 6.92; N, 17.49; Found: C, 42.35; H, 7.21; N, 17.54.

EXAMPLE 14

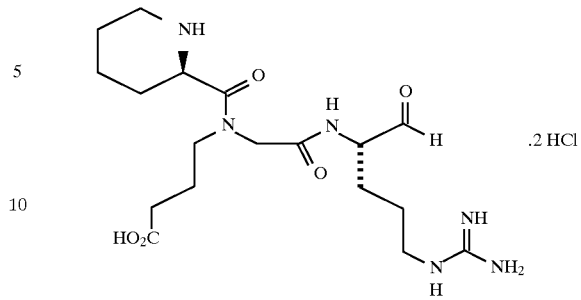

Synthesis of D-hPro-N(CH$_2$CH$_2$CH$_2$COOH)Gly-ArgH.2HCl

A) Preparation of N(CH$_2$CH$_2$CH$_2$COOEt)Gly-O-t-Bu

By a method substantially equivalent to that described in Example 2-A, 13.6 g (55%) of N(CH$_2$CH$_2$CH$_2$COOEt)Gly-O-t-Bu were prepared from t-butyl bromoacetate and ethyl 4-amino-butyrate hydrochloride.

$^1$H NMR

B) Preparation of Cbz-D-hPro-N(CH$_2$CH$_2$CH$_2$COOEt)-Gly-O-t-Bu

By a method substantially equivalent to that described in Example 1-B, 6.1 g (33%) of Cbz-D-hPro-N(CH$_2$CH$_2$CH$_2$COOEt)Gly-O-t-Bu were prepared from Cbz-D-hPro-OH and N(CH$_2$CH$_2$CH$_2$COOEt)Gly-O-t-Bu.

$^1$H NMR

FD-MS, m/e 538 (M$^+$)

C) Preparation of Cbz-D-hPro-N(CH$_2$CH$_2$CH$_2$COOBn)-Gly-O-t-Bu

To a solution of Cbz-D-hPro-N(CH$_2$CH$_2$CH$_2$COOEt)Gly-O-t-Bu (7.4 g, 15 mmol) in dioxane (200 mL) was added a solution of LiOH (0.8 g, 19 mmol) in H$_2$O (100 mL). The mixture was allowed to stir for 2 hours at room temperature and was then concentrated to a volume of 10 mL. The residue was diluted to 100 mL with H$_2$O and washed with diethyl ether. The aqueous layer was acidified to pH 3 with 5N HCl and then was extracted twice with ethyl acetate (50 mL). The organic layer was dried (MgSO$_4$) and concentrated in vacuo to give a colorless oil. The oil was dissolved in dichloromethane and to this solution was added benzyl alcohol (2.5 mL, 23 mmol), dimethylaminopyridine (1.8 g, 15 mmol) and dicyclohexylcarbodiimide (3.1 g, 15 mmol). After stirring for 16 hours at room temperature, a white precipitate was removed by filtration and the filtrate was concentrated in vacuo. The residue was chromatographed over silica gel, eluting with a step gradient of hexanes through 50% ethyl acetate/hexanes. Fractions containing product (based on TLC) were combined and concentrated to give 6.1 g (74%) of a colorless oil.

$^1$H NMR

FD-MS, m/e 552 (M$^+$)

Analysis for C$_{31}$H$_4$N$_2$O$_{07}$: Calc: C, 67.37; H, 7.30. N, 5.07; Found: C, 67.48; H, 7.46. N, 4.83.

D) Preparation of Cbz-D-hPro-N(CH$_2$CH$_2$CH$_2$COOBn)-Gly-OH

By a method substantially equivalent to that described in Example 2-C, 5.2 g (98%) of Cbz-D-hPro-N(CH$_2$CH$_2$CH$_2$COOBn)Gly-OH were prepared.

$^1$H NMR

FD-MS, m/e 497 (M$^+$)

E) Preparation of Cbz-D-hPro-N(CH$_2$CH$_2$CH$_2$COOBn)-Gly-Arg(Cbz)lactam

By a method substantially equivalent to that described in Example 1-G, 4.9 g (70%) of Cbz-D-hPro-N (CH₂CH₂CH₂COOBn)Gly-Arg(Cbz) lactam were prepared from Cbz-D-hPro-N(CH₂CH₂CH₂COOBn)Gly-OH and Arg(Cbz)lactam.2HCl.
¹H NMR
FD-MS, m/e 770 (MH⁺)
Analysis for $C_{41}H_{48}N_6O_9$: Calc: C, 64.05; H, 6.29. N, 10.93; Found: C, 64.26; H, 6.37. N, 10.69.

F) Preparation of D-hPro-N(CH₂CH₂CH₂COOH)Gly-ArgH.2HCl

By a method substantially equivalent to that described in Example 5-E, 1.1 g (91%) of D-hPro-N(CH₂CH₂CH₂COOH)Gly-ArgH.2HCl were prepared. One gram of this material was purified by RPHPLC method B to give 0.1 g (10%) of pure product.
¹H NMR
FD-MS, m/e 413 (MH⁺)
Analysis for $C_{18}H_{32}N_6O_5$.2HCl.1H₂O: Calc: C, 42.95; H, 7.21; N, 16.69; Found: C, 42.84; H, 6.82; N, 16.65.

EXAMPLE 15

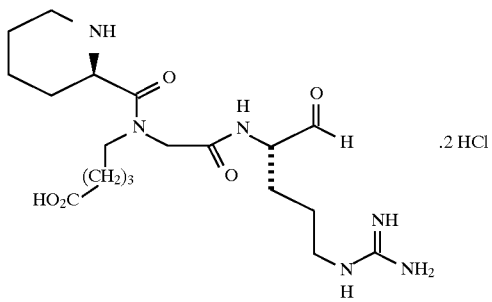

Synthesis of D-hPro-N(CH₂CH₂CH₂CH₂COOH) Gly-ArgH.2HCl

A) Preparation of N(CH₂CH₂CH₂CH₂COOEt)Gly-O-t-Bu

By a method substantially equivalent to that described in Example 2-A, 5.8 g (31%) of N(CH₂CH₂CH₂CH₂COOEt)Gly-O-t-Bu were prepared from glycine t-butyl ester hydrochloride and ethyl bromovalerate.
¹H NMR B) Preparation of Cbz-D-hPro-N(CH₂CH₂CH₂CH₂COOEt)-Gly-O-t-Bu By a method substantially equivalent to that described in Example 1-B, 8.0 g (72%) of Cbz-D-hPro-N(CH₂CH₂CH₂CH₂COOEt)Gly-O-t-Bu were prepared.
¹H NMR
FD-MS, m/e 505 (M⁺)

C) Preparation of Cbz-D-hPro-N(CH₂CH₂CH₂CH₂COOBn)-Gly-O-t-Bu

By a method substantially equivalent to that described in Example 14-C, 5 g (60%) of Cbz-D-hPro-N(CH₂CH₂CH₂CH₂COOBn)Gly-O-t-Bu were prepared.
¹H NMR
FD-MS, m/e 566 (M⁺)
Analysis for $C_{32}H_{42}N_2O_7$: Calc: C, 67.82; H, 7.47. N, 4.94; Found: C, 68.05; H, 7.21. N, 5.15.

D) Preparation of Cbz-D-hPro-N(CH₂CH₂CH₂CH₂COOBn)-Gly-OH

By a method substantially equivalent to that described in Example 2-C, 4.3 g (97%) of Cbz-D-hPro-N(CH₂CH₂CH₂CH₂COOBn)Gly-OH were prepared.
¹H NMR
FD-MS, m/e 511 (M⁺)

E) Preparation of Cbz-D-hPro-N(CH₂CH₂CH₂CH₂COOBn)-Gly-Arg(Cbz)lactam

By a method substantially equivalent to that described in Example 1-G, 4.1 g (66%) of Cbz-d-hPro-N(C₂CH₂CH₂Ch₂COOBn)Gly-Arg lactam were prepared from Cbz-D-hPro-N(CH₂CH₂CH₂CH₂COOBn) Gly-OH and Arg(Cbz) lactam.2HCl.
¹H NMR
FD-MS, m/e 784 (M⁺)

F) Preparation of D-hPro-N(CH₂CH₂CH₂CH₂COOH)-Gly-ArgH.2HCl

By a method substantially equivalent to that described in Example 5-E, 1.97 g (79%) of D-hPro-N(CH₂CH₂CH₂CH₂COOH)Gly-ArgH.2HCl were prepared. One gram of this material was purified by RPHPLC method B to give 0.24 g (24%) of pure product.
¹H NMR
FD-MS, m/e 427.3 (MH⁺)
Analysis for $C_{19}H_{34}N_6O_5$.2HCl: Calc: C, 45.69; H, 7.27; N, 16.83; Found: C, 46.01; H, 7.26; N, 17.13.

EXAMPLE 16

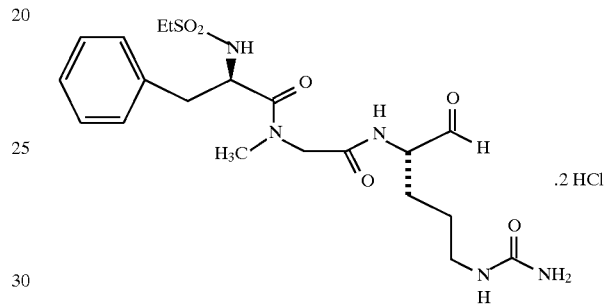

Synthesis of EtSO₂—D-Phe-N(Me)Gly-ArgH.2HCl (N-(ethylsulfonyl)-D-phenylalanyl-N-methylglycyl-L-argininal dihydrochloride)

A) Preparation of EtSO₂—D-Phe-OH

To a stirring suspension of D-Phe-OH (50 g, 300 mmol) in tetrahydrofuran (400 mL) was added N,O-bis(trimethylsilyl)acetamide (92 g, 450 mmol). Upon clarification the solution was cooled to −78° C. and N,N-diisopropylethylamine (57.5 mL, 330 mmol) was added, followed by ethanesulfonyl chloride (31.3 mL, 330 mmol). The cold bath was left unattended and the mixture was allowed to warm slowly to room temperature. After 16 hours, water (100 mL) was added and then the organic solvent was removed in vacuo. The aqueous phase was diluted with 1N NaOH and washed twice with diethyl ether. The aqueous phase was then acidified to pH 3 with conc. HCl and extracted three times with ethyl acetate. The combined ethyl acetate extracts were dried (Na₂SO₄), filtered and concentrated in vacuo to give 70 g (91%) of a yellow foam.
¹H NMR
FD-MS, m/e 258 (MH⁺)

B) Preparation of EtSO₂—D-Phe-N(Me)Gly-OEt

By a method substantially equivalent to that described in Example 1-B, 17.5 g (86%) of EtSO₂—D-Phe-N(Me)Gly-OEt were prepared from EtSO₂—D-Phe-OH and N(Me)Gly-OEt.
¹H NMR
FD-MS, m/e 356 (M⁺)
Analysis for $C_{16}H_{24}N_2O_5S$: Calc: C, 53.91; H, 6.79; N, 7.86; Found: C, 53.94; H, 6.73; N, 7.79.

C) Preparation of EtSO₂—D-Phe-N(Me)Gly-OH

By a method substantially equivalent to that described in Example 1-C, 13.8 g (87%) of EtSO₂—D-Phe-N(Me)Gly-OH were prepared.

¹H NMR
FD-MS, m/e 329 (MH⁺)
Analysis for $C_{14}H_{20}N_2O_5S$: Calc: C, 51.21; H, 6.14; N, 8.53; Found: C, 51.50; H, 6.08; N, 8.51.

D) Preparation of EtSO₂—D-Phe-N(Me)Gly-Arg(Cbz) lactam

By a method substantially equivalent to that described in Example 1-G, 7.5 g (63%) of EtSO₂—D-Phe-N(Me)Gly-Arg(Cbz)lactam were prepared from EtSO₂—D-Phe-N(Me)Gly-OH and Arg(Cbz)lactam.2HCl.

¹H NMR
FD-MS, m/e 601 (M⁺)
Analysis for $C_{28}H_{36}N_6O_7S$: Calc: C, 55.99; H, 6.04; N, 13.99; Found: C, 55.69; H, 5.97; N, 13.69.

E) Preparation of EtSO₂—D-Phe-N(Me)Gly-ArgH.HCl

By a method substantially equivalent to that described in Example 5-E, 2.3 g (60%) of EtSO₂—D-Phe-N(Me)Gly-ArgH.2HCl were prepared. Purification by HPLC was unnecessary.

¹H NMR
FD-MS, m/e 469 (MH⁺)
Analysis for $C_{20}H_{32}N_6O_5S.HCl.H_2O$: Calc: C, 45.93; H, 6.74; N, 16.07; Found: C, 45.55; H, 6.57; N, 16.17.

EXAMPLE 17

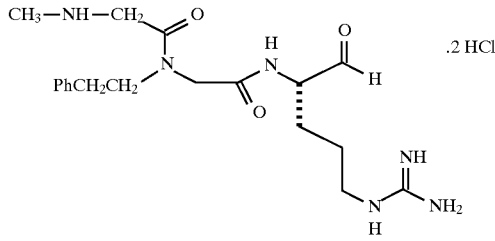

Synthesis of Sar-N(CH₂CH₂Ph)Gly-ArgH.2HCl
A) Preparation of Sar-N(CH₂CH₂Ph)Gly-ArgH.2HCl By methods substantially equivalent to those described in Example 8, 1.75 g of Sar-N(CH₂CH₂Ph)Gly-ArgH.2HCl were prepared from Cbz-sarcosine. 1.1 g of this material were purified by RPHPLC method B to give 0.99 g (90%) of pure product.

¹H NMR
FD-MS, m/e 391 (MH⁺)
Analysis for $C_{19}H_{30}N_6O_3.2HCl$: Calc: C, 49.25; H, 6.96; N, 18.14; Found: C, 48.99; H, 6.96; N, 17.96.

EXAMPLE 18

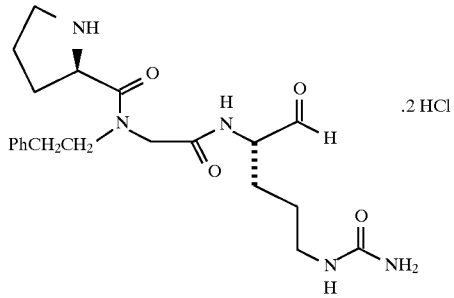

Synthesis of D-Pro-N(CH₂CH₂Ph)Gly-ArgH.2HCl
A) Preparation of D-Pro-N(CH₂CH₂Ph)Gly-ArgH.2HCl By methods substantially equivalent to those described in Example 8, 2.38 g of D-Pro-N(CH₂CH₂Ph)Gly-ArgH.2HCl were prepared from Cbz-D-proline. Purification by HPLC was unnecessary.

¹H NMR
FD-MS, m/e 417 (MH⁺)
Analysis for $C_{21}H_{32}N_6O_3.3HCl.H_2O$: Calc: C, 46.37; H, 6.86; N, 15.45; Found: C, 46.77; H, 6.93; N, 15.32.

EXAMPLE 19

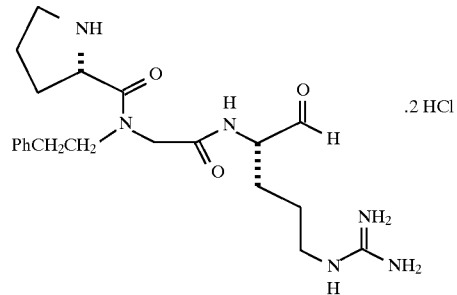

Synthesis of L-Pro-N(CH₂CH₂Ph)Gly-ArgH.2HCl
A) Preparation of L-Pro-N(CH₂CH₂Ph)Gly-ArgH.2HCl By methods substantially equivalent to those described in Example 8, 1.56 g of L-Pro-N(CH₂CH₂Ph)Gly-ArgH.2HCl were prepared from Cbz-L-proline. One gram of this material was purified by RPHPLC method B to give 0.56 g (56%) of pure product.

¹H NMR
FD-MS, m/e 417 (MH⁺)
Analysis for $C_{21}H_{32}N_6O_3.2HCl.2H_2O$: Calc: C, 48.00; H, 7.29; N, 15.99; Found: C, 47.78; H, 7.14; N, 16.12.

In the same way as described above can be prepared the following compounds:
EtSO₂—D-Phe-N(Ph)Gly-ArgH
EtSO₂—D-Phe-N(PhCH₂CH₂)Gly-ArgH
EtSO₂—D-Phg-N(Me)Gly-ArgH
EtSO₂—D-Phg-N(Ph)Gly-ArgH
EtSO₂—D-Phg-N(PhCH₂CH₂)Gly-ArgH
EtSO₂—D-Cha-N(Me)Gly-ArgH
EtSO₂—D-Cha-N(Ph)Gly-ArgH
EtSO₂—D-Cha-N(PhCH₂CH₂)Gly-ArgH
EtSO₂—D-Chg-N(Me)Gly-ArgH
EtSO₂—D-Chg-N(Ph)Gly-ArgH
EtSO₂—D-Chg-N(PhCH₂CH₂)Gly-ArgH
HO₂CCH₂SO₂—D-Phe-N(Me)Gly-ArgH
HO₂CCH₂SO₂—D-Phe-N(Ph)Gly-ArgH
HO₂CCH₂SO₂—D-Phe-N(PhCH₂CH₂)Gly-ArgH
HO₂CCH₂SO₂—D-Phg-N(Me)Gly-ArgH
HO₀₂CCH₂SO₂—D-Phg-N(Ph)Gly-ArgH
HO₂CCH₂SO₂—D-Phg-N(PhCH₂CH₂)Gly-ArgH
HO₂CCH₂SO₂—D-Cha-N(Me)Gly-ArgH
HO₂CCH₂SO₂—D-Cha-N(Ph)Gly-ArgH
HO₀₂CCH₂S₂—D-Cha-N(PhCH₂CH₂)Gly-ArgH
HO₂CCH₂SO₂—D-Chg-N(Me)Gly-ArgH
HO₂CCH₂SO₂—D-Chg-N(Ph)Gly-ArgH
HO₂CCH₂SO₂—D-Chg-N(PhCH₂CH₂)Gly-ArgH
HO₂CCH₂—D-Phe-N(Me)Gly-ArgH
HO₂CCH₂—D-Phe-N(Ph)Gly-ArgH
HO₂CCH₂—D-Phe-N(PhCH₂CH₂)Gly-ArgH
HO₂CCH₂—D-Phg-N(Me)Gly-ArgH
HO₂CCH₂—D-Phg-N(Ph)Gly-ArgH
HO₂CCH₂—D-Phg-N(PhCH₂CH₂)Gly-ArgH
HO₂CCH₂—D-Cha-N(Me)Gly-ArgH
HO₂CCH₂—D-Cha-N(Ph)Gly-ArgH
HO₂CCH₂—D-Cha-N(PhCH₂CH₂)Gly-ArgH HO$_2$CCH$_2$—D-Chg-N(Me)Gly-ArgH
HO$_2$CCH$_2$—D-Chg-N(Ph)Gly-ArgH
HO$_2$CCH$_2$—D-Chg-N(PhCH$_2$CH$_2$)Gly-ArgH
CH$_3$—D-Phe-N(Me)Gly-ArgH
CH$_3$—D-Phe-N(Ph)Gly-ArgH
CH$_3$—D-Phe-N(PhCH$_2$CH$_2$)Gly-ArgH
CH$_3$—D-Phg-N(Me)Gly-ArgH
CH$_3$—D-Phg-N(Ph)Gly-ArgH
CH$_3$—D-Phg-N(PhCH$_2$CH$_2$)Gly-ArgH
CH$_3$—D-Cha-N(Me)Gly-ArgH
CH$_3$—D-Cha-N(Ph)Gly-ArgH
CH$_3$—D-Cha-N(PhCH$_2$CH$_2$)Gly-ArgH
CH$_3$—D-Chg-N(Me)Gly-ArgH
CH$_3$—D-Chg-N(Ph)Gly-ArgH
CH$_3$—D-Chg-N(PhCH$_2$CH$_2$)Gly-ArgH
1-Piq-N(Me)Gly-ArgH
1-Piq-N(Ph)Gly-ArgH
1-Piq-N(PhCH$_2$CH$_2$)Gly-ArgH
3-Piq-N(Me)Gly-ArgH
3-Piq-N(Ph)Gly-ArgH
3-Piq-N(PhCH$_2$CH$_2$)Gly-ArgH The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis. Further, the compounds of the present invention are believed to be orally active.

The invention in one of its aspects provides a method of inhibiting thrombin in mammals comprising administering to a mammal in need of treatment an effective (thrombin inhibiting) dose of a compound of Formula I.

The thrombin inhibition contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disease states in which the compounds have a potential utility are in treatment or prophylaxis of thrombosis and hypercoagulability in blood and tissues. Disease states in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in prophylaxis of atherosclerotic diseases such as coronary arterial disease, cerebral arterial disease and peripheral arterial disease. Further, the compounds are expected to be useful together with thrombolytics in myocardial infarction. Further, the compounds have expected utility in the treatment or prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, and inflammatory diseases, including arthritis and diabetes. The anticoagulant compound is administered orally, or parenterally, e.g., by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, and the condition being treated.

A typical daily dose for each of the above utilities is between about 0.01 mg/kg and about 1000 mg/kg. The dose regime may vary, e.g., for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent, e.g., tissue plasminogen activator (tPA), modified tPA, streptokinase or urokinase. In cases when clot formation has occurred and an artery or vein is blocked, either partially or totally, a clot lysing agent is usually employed. A compound of the invention can be administered prior to or along with the lysing agent or subsequent to its use alone and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the reoccurrence of clot formation.

The method of this invention is also practiced in conjunction with aspirin. A compound of the invention can be administered prior to or along with aspirin or subsequent to its use to prevent the reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of Formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent, e.g., physiological saline (0.9%), 5% dextrose, Ringer's solution, and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Therefore, another embodiment of the present invention is a pharmaceutical formulation comprising an effective amount of a compound of Formula I or a pharmaceutically acceptable salt or solvate thereof in association with a pharmaceutically acceptable carrier, diluent or excipient therefor.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like. The compositions of this invention may be formulated so as to provide quick, sustained, or delayed release of the active ingredient after administration to the patient by employing procedures well known in the art.

The following formulation examples are illustrative only and are not intended to limit the scope of the invention in any way. "Active ingredient," of course, means a compound according to Formula I or a pharmaceutically acceptable salt or solvate thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
| --- | --- |
| Starch | 59 mg |

| | |
|---|---|
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 mL dose, are made as follows:

| | |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 mL |

The solution of the above ingredients generally is administered intravenously to a subject at a rate of 1 mL per minute.

The compounds provided by the invention (Formula I) are orally active and selectively inhibit the action of thrombin in mammals.

The ability of the compounds of the present invention to be an effective and orally active thrombin inhibitor is evaluated in one or more of the following assays.

The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide.

The assay is carried out by mixing 50 μL buffer (0.03M Tris, 0.15M NaCl, pH 7.4) with 25 μL of bovine thrombin or human thrombin solution (0.21 mg/mL of thrombostat bovine thrombin, Parke-Davis, or purified human thrombin, Enzyme Research Laboratories, South Bend, Ind., at about 8 NIH units/mL, in the same buffer) and 25 μL of test compound in a solvent (in 50% aqueous methanol, v:v). The 150 μL of an aqueous solution of the chromogenic substrate (at 0.25 mg/mL) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

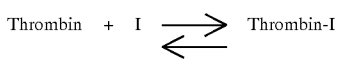

$$Kass = \frac{[Thrombin-I]}{[(Thrombin) \times (I)]}$$

Kass is calculated for a range of concentrations of test compounds and the mean value is reported in units of liter per mole.

By substantially following the procedures described above for human thrombin, and using other human blood coagulation system serine proteases and proteases of the fibrinolytic system with the appropriate chromogenic substrates, identified below, selectivity of the compounds of the present invention with respect to the coagulation factor serine proteases and with respect to the fibrinolytic system serine proteases are evaluated as well as their substantial lack of interference with serine proteases of the fibrinolytic system. Thrombin inhibitors preferably should spare fibrinolysis induced by urokinase, tissue plasminogen activator (t-PA) and streptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952 incorporated by reference herein in its entirety. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from Kabi Vitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Table 1 which follows lists the Kass values obtained with the indicated compound represented by the Formula I.

TABLE 1

Inhibition Properties

| Example | Enzyme Kass (L/mol × 10$^6$) | | | | |
|---|---|---|---|---|---|
| | Human Thrombin | Xa | Trypsin | Plasmin | t-PA |
| 1 | 22 | 0.13 | 0.88 | 0.031 | 0.0039 |
| 2 | 33 | 0.039 | 1.3 | 0.013 | 0.005 |
| 3 | 34 | 0.084 | 2.4 | 0.045 | 0.004 |
| 4 | 9.7 | 0.074 | 0.5 | 0.031 | 0.001 |
| 5 | 24 | 0.060 | 1.6 | 0.050 | 0.002 |
| 6 | 16 | 0.071 | 5.9 | 0.059 | 0.004 |
| 7 | 11 | 0.25 | 10 | 0.13 | 0.010 |
| 8 | 87 | 4.4 | 2.7 | 0.44 | 0.009 |
| 9 | 24 | 0.31 | 6.0 | 0.12 | 0.006 |
| 10 | 5.4 | 0.22 | 5.8 | 0.33 | 0.007 |
| 11 | 16 | 0.21 | 1.1 | 0.036 | 0.0039 |
| 12 | 3.3 | 0.14 | 0.55 | 0.060 | 0.0064 |
| 13 | 0.83 | 0.051 | 0.48 | 0.015 | 0.001 |
| 14 | 1.2 | 0.062 | 0.60 | 0.016 | 0.001 |
| 15 | 1.8 | 0.078 | 0.99 | 0.020 | 0.001 |
| 16 | 37 | 3.3 | 22 | 1.5 | 1.2 |
| 17 | 2.9 | 2.2 | 0.38 | 0.20 | 0.001 |
| 18 | 5.1 | 0.47 | 1.1 | 0.34 | 0.001 |
| 19 | 0.64 | 0.11 | 0.22 | 0.22 | <0.001 |

Materials

Dog plasma is obtained from conscious mixed-breed hounds (either sex Hazelton-LRE, Kalamazoo, Mich., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased form Leo Pharmaceuticals, Denmark, as 2200 Ploug units/vial. Streptokinase is purchased from Hoechst-Roussel Pharmaceuticals, Somerville, N.J.

Methods

Effects on Lysis of Human Plasma Clots by t-PA

Human plasma clots are formed in micro test tubes by adding 50 μL thrombin (73 NIH unit/mL) to 100 μL human plasma which contains 0.0229 μCi 125-iodine labeled fibrinogen. Clot lysis is studied by overlaying the clots with 50 μL of urokinase or streptokinase (50, 100, or 1000 unit/mL) and incubating for 20 hours at room temperature. After incubation the tubes are centrifuged in a Beckman Microfuge. 25 μL of supernate is added into 1.0 mL volume of 0.03M tris/0.15M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 ug/mL concentrations. Rough approximations of IC50 values are estimated by linear extrapolations from data points to a value which would represent 50 percent of lysis for that particular concentration of fibrinolytic agent.

Anticoagulant Activity

Materials

Dog plasma and rat plasma is obtained from conscious mixed-breed hounds (either sex, Hazelton-LRE, Kalamazoo, Mich., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/ plasmin free from American Diagnostica, Greenwich, Conn. Coagulation reagents ACTIN, Thromboplastin, and Human plasma are from Baxter Healthcare Corp., Dade Division, Miami, Fla. Bovine thrombin from Parke-Davis (Ann Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent to 0.05 mL test plasma. The activated partial thromboplastin time (APTT) is measured by incubation of 0.05 mL test plasma with 0.05 mL Actin reagent for 120 seconds followed by 0.05 mL CaCl$_2$ (0.02M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous shunt model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood circulated through the shunt for 15 minutes before the thread is carefully removed and weighed. The weight of a wet thread is subtracted from the total weight of the thread and thrombus (see J. R. Smith, *Br. J. Pharmacol.*, 77,29 (1982)).

FeCl$_3$ model of arterial injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. FeCl$_3$ hexahydrate is dissolved in water and the concentration (20%) is expressed in terms of the actual weight of FeCl$_3$ only. To injure the artery and induce thrombosis, 2.85 μl is pipetted into the cuff to bathe the artery above the thermocouple probe. Arterial occlusion is indicated by a rapid drop in temperature. The time to occlusion is reported in minutes and represented the elapsed time between application of FeCl$_3$ and the rapid drop in vessel temperature (see K. D. Kurz, *Thromb. Res.*, 60, 269 (1990)).

Spontaneous thrombolysis model

In vitro data suggested that the peptide thrombin inhibitors inhibit thrombin and other serine proteases, such as plasmin and tissue plasminogen activator. To assess if the compounds inhibited fibrinolysis in vivo, the rate of spontaneous thrombolysis is determined by implanting a labeled whole blood clot into the pulmonary circulation. Rat blood (1 mL) is mixed rapidly with bovine thrombin (4 IU, Parke Davis) and $^{125}$I human fibrogen (5 μCi, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected } cpm - \text{lung } cpm)}{\text{injected } cpm} \times 100$$

The fibrinolytic dissolution of the implanted clot occurs time-dependently (see J. P. Clozel, *Cardiovas. Pharmacol.*, 12, 520 (1988)).

Coagulation parameters

Plasma thrombin time (TT) and activated partial thromboplastin time (APTT) are measured with a fibrometer. Blood is sampled from a jugular catheter and collected in syringe containing sodium citrate (3.8%, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and CaCl$_2$ (0.01 mL, 0.025M) is added to start coagulation. Assays are done in duplicate and averaged.

Index of Bioavailability

A measure of bioactivity, plasma thrombin time (TT), served as a substitute for the assay of parent compound on the assumption that increments in TT resulted from thrombin inhibition by parent only. The time course of the effect of the thrombin inhibitor upon TT is determined after i.v. bolus administration to anesthetized rats and after oral treatment of fasted conscious rats. Due to limitations of blood volume and the number of points required to determine the time course from time of treatment to the time when the response returned to pretreatment values, two populations of rats are used. Each sample population represented alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{AUC\,po}{AUC\,iv} \times \frac{\text{Dose } iv}{\text{Dose } po} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the FeCl$_3$ model of arterial injury and in the spontaneous thombosis model. Bolus injection volume is 1 mL/kg for i.v., and 5 mL/kg for p.o. and infusion volume is 3 mL/hr.

Statistics

Results are expressed as means ±SEM. One-way analysis of variance is used to detect statistically significant differences and then Dunnett's test is applied to determine which means are different. Significance level for rejection of the null hypothesis of equal means is P<0.05.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66°–74° F.; 45–50% relative humidity; and lighted from 0600–1800 hours.

Pharmacokinetic model

Test compound is formulated immediately prior to dosing by dissolving in sterile 0.9% saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are derivatized with dinitrophenylhydrazine and analyzed by HPLC (Zorbax SB-C8 column) eluting with methanol/500 mM sodium acetate adjusted to pH 7 with phosphoric acid (60:40, v/v). Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound at Tmax, Cmax; plasma half-life, t0.5; area under the curve, A.U.C.; and fraction of test compound absorbed, F.

Canine Model of Coronary Artery Thrombosis

Surgical preparation and instrumentation of the dogs are as described in Jackson, et al., Circulation, 82, 930–940 (1990). Mixed-breed hounds (aged 6–7 months, either sex, Hazelton-LRE, Kalamazoo, Mich., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon®-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50% inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 minutes and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/h is begun simultaneously with an infusion of thrombolytic agent (e.g. tissue plasminogen activator, streptokinase, APSAC). Reperfusion is followed for 3 hours after administration of test compound. Reocclusion of coronary arteries after successful thrombolysis is defined as zero CBF which persisted for $\geq$30 minutes.

Hematolocy and template bleeding time determinations

Whole blood cell counts, hemoglobin, and hematocrit values are determined on a 40-$\mu$l sample of citrated (3.8%) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 minutes), 60 minutes into infusion, at conclusion of administration of the test compound (120 minutes), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean ±SEM. All studies are conducted in accordance with the guiding principles of the American Physiological Society. Further details regarding the procedures are described in Jackson, et al., J. Cardiovasc. Pharmacol., 21, 587–599 (1993).

TABLE 2

| | Human Plasma Anticoagulation 2 × Clotting time (na/mL) | | | % oral/i.v. |
|---|---|---|---|---|
| Example | TT | APTT | PT | activity (Rat) |
| 1 | 160 | 2,800 | 4,800 | 37 |
| 2 | 160 | 2,600 | 5,000 | NT |
| 3 | 77 | 2,100 | 2,000 | NT |
| 4 | 230 | 12,000 | 14,000 | NT |
| 5 | 100 | 3,800 | 4,900 | NT |
| 6 | 170 | 3,200 | 2,600 | 22 |
| 7 | 120 | 3,700 | 4,400 | NT |
| 8 | 64 | 6,600 | 2,000 | 17 |
| 9 | 55 | 2,200 | 3,000 | NT |
| 10 | 230 | 4,100 | 6,900 | NT |
| 11 | 120 | 2,200 | 3,100 | NT |
| 12 | 370 | 4,900 | 8,200 | NT |
| 13 | 800 | 21,000 | 27,000 | NT |
| 14 | 700 | 20,000 | 30,000 | NT |
| 15 | 670 | 15,000 | 21,000 | NT |
| 16 | 30 | 1,200 | 1,600 | NT |
| 17 | 150 | 2,200 | 2,700 | NT |
| 18 | 170 | 3,300 | 3,900 | NT |
| 19 | 490 | 10,000 | 10,000 | NT |

We claim:

1. A compound having the formula

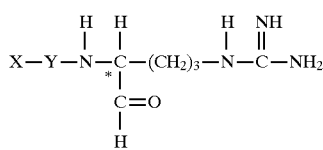

wherein

X is prolinyl, homoprolinyl,

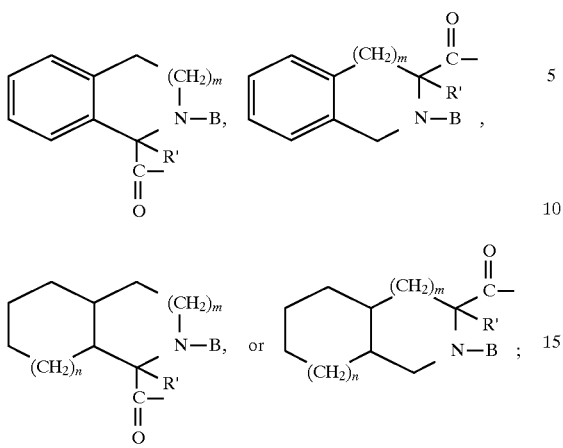

B is hydrogen or $C_1$–$C_4$ alkyl;
R' is hydrogen or $C_1$–$C_4$ alkyl;
m is 0, 1, or 2;
n is 0, 1, or 2;

R is $C_1$–$C_6$ alkyl, $C_3$–$C_8$ cycloalkyl, or —$(CH_2)_p$—L—$(CH_2)_q$—T'; where p is 0, 1, 2, 3, or 4, L is a bond, —O—, —S—, or —NH—, q is 0, 1, 2 or 3, and T' is hydrogen, $C_1$–$C_4$ alkyl, $C_3$–$C_8$ cycloalkyl, —COOH, —$CONH_2$, or Ar, where Ar is unsubstituted or substituted aryl where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

Z is hydrogen, $C_1$–$C_4$ alkyl, $C_1$–$C_4$ alkoxy, hydroxy, halo, or $R_aSO_2NH$—, where $R_a$ is $C_1$–$C_4$ alkyl;

provided that R is not hydrogen and provided that R is not $C_1$–$C_6$ alkyl when X is and pharmaceutically acceptable salts and solvates thereof.

2. A compound of claim 1 where X is homoprolinyl, 1- or 3-Tiq, or 1- or 3-Piq, and pharmaceutically acceptable salts and solvates thereof.

3. The compound of claim 2 which is D-homoprolyl-N-(2-phenylethyl)glycyl-L-argininal and pharmaceutically acceptable salts and solvates thereof.

4. A pharamaceutical formulation comprising a compound of claim 1 in association with a pharmaceutically acceptable carrier, diluent, or excipient therefor.

5. A compound of claim 2 where R is $C_1$–$C_6$ alkyl or —$(CH_2)_p$—L—$(CH_2)_q$—Ar, and pharmaceutically acceptable salts and solvates thereof.

6. A compound of claim 4 where R is methyl, ethyl or n-propyl, and pharmaceutically acceptable salts and solvates thereof.

7. A compound of claim 4 where R is phenylethyl, and pharmaceutically acceptable salts and solvates thereof.

8. A formulation of claim 2 containing a compound where R is methyl, ethyl or n-propyl, or a pharamaceutically acceptable salt or solvate thereof.

9. A formulation of claim 2 containing a compound where R is phenylethyl, or a pharmaceutically acceptable salt or solvate thereof.

* * * * *